United States Patent
Nan et al.

(10) Patent No.: US 11,192,916 B2
(45) Date of Patent: Dec. 7, 2021

(54) PENTACYCLIC TRITERPENE COMPOUND AND PREPARATION METHOD THEREFOR, AND PHARMACEUTICAL COMPOSITION AND USE THEREOF

(71) Applicant: SHANGHAI INSTITUTE OF MATERIA MEDICA, CHINESE ACADEMY OF SCIENCES, Shanghai (CN)

(72) Inventors: Fajun Nan, Shanghai (CN); Xin Xie, Shanghai (CN); Chenlu Zhang, Shanghai (CN); Shimeng Guo, Shanghai (CN); Yangming Zhang, Shanghai (CN); Siwei Wang, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/648,123

(22) PCT Filed: Sep. 17, 2018

(86) PCT No.: PCT/CN2018/106012
§ 371 (c)(1),
(2) Date: Mar. 17, 2020

(87) PCT Pub. No.: WO2019/052560
PCT Pub. Date: Mar. 21, 2019

(65) Prior Publication Data
US 2020/0231623 A1 Jul. 23, 2020

(30) Foreign Application Priority Data
Sep. 18, 2017 (CN) .......................... 201710841681.8

(51) Int. Cl.
*C07J 63/00* (2006.01)
(52) U.S. Cl.
CPC .................................. *C07J 63/008* (2013.01)
(58) Field of Classification Search
CPC ...................................................... C07J 63/008
USPC ...................................................... 514/182
See application file for complete search history.

(56) References Cited

U.S. PATENT DOCUMENTS

2005/0049230 A1   3/2005   Henrich et al.

FOREIGN PATENT DOCUMENTS

| CN | 101 337 984 A | 1/2009 | |
| CN | 101519423 A | 9/2009 | |
| CN | 104725456 | 6/2015 | |
| CN | 104877000 | 9/2015 | |
| CN | 104910239 | 9/2015 | |
| EP | 0943620 | 9/1999 | |
| JP | 2003-508543 A | 3/2003 | |
| RU | 2 430 105 C1 | 9/2011 | |
| WO | WO-01/18029 A1 | 3/2001 | |
| WO | WO-2011/150286 A2 | 12/2011 | |
| WO | WO-2014/071506 A1 | 5/2014 | |
| WO | WO-2014/105926 A1 | 7/2014 | |
| WO | WO-2015/135474 A1 | 9/2015 | |
| WO | WO 2015135449 | * 9/2015 | ............. C07J 63/00 |
| WO | WO-2016/086453 A1 | 6/2016 | |
| WO | WO-2017/017630 A1 | 2/2017 | |
| WO | WO-2017/068057 A1 | 4/2017 | |

OTHER PUBLICATIONS

Extended European search report issued in European patent application No. 18856706.9, dated May 10, 2021.
Genet, Cédric, et al., "Structure—Activity Relationship Study of Betulinic Acid, A Novel and Selective TGR5 Agonist, and Its Synthetic Derivatives: Potential Impact in Diabetes" Journal of Medicinal Chemistry, vol. 53, No. 1, Jan. 14, 2010, pp. 178-190.
Japanese Office Action dated Jun. 7, 2021 issued in Japanese patent application No. 2020-537276, with English translation.
Wang, Xiao-yin, et al., "highly lipophilic 3-epi-betulinic acid derivatives as potent and selective TGR5 agonists with improved cellular efficacy" Acta Pharmacologica Sinica 2014, vol. 35, pp. 1463-1472.
Protiva J., et al., "Reaction of Amides of 28-Lupanoic Acid With Lead Tetraacetate and Iodine Mass Spectra of 12-Lupene Derivatives", Collection Czechoslov. Chem. Common. 1976, vol. 41, pp. 1200-1207.
Protiva, J., et al., "Unusual Course of Photolysis of 3β-Acetoxy-28-Nitrosyloxylupane. Synthesis of Triterpenic N-Oxides and Hydroxamic Acids", Collection Czechoslov. Chem. Common. 1977, vol. 42, pp. 1220-1228.

(Continued)

*Primary Examiner* — Nizal S Chandrakumar
(74) *Attorney, Agent, or Firm* — Faegre Drinker Biddle & Reath LLP

(57) ABSTRACT

Disclosed are a pentacyclic triterpene compound as shown in general formula (I) and a preparation method therefor. The compound has an effective antagonistic effect on FXR receptors.

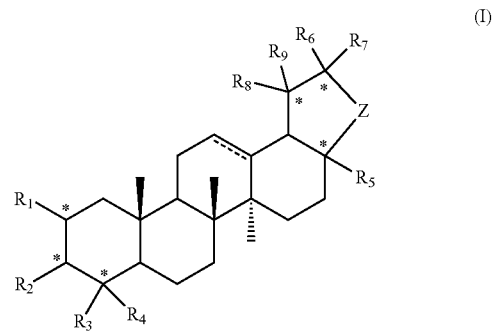

4 Claims, No Drawings

(56) References Cited

OTHER PUBLICATIONS

Drefahl, G., et al., "Über Redoktionsprodokte verschiedener Triterpenoxime und Triterpensäureamide", Institote für Organische Chemieond Biochemieder Universität Jena 1960, vol. 93, pp. 1967-1975.

International Search Report and Written Opinion for PCT/CN2018/106012, ISA/CN, dated Dec. 4, 2018, 8 pages.

Chen, Dongyin et al. "Discovery of Pentacyclic Triterpene 3β-ester Derivatives as a New Class of Cholesterol Ester Transfer Protein Inhibitors" European Journal of Medicinal Chemistry, vol. 139, Aug. 4, 2017, pp. 201-213.

Chen, Jun et al. "Pentacyclic Triterpenes. Part 3: Synthesis and Biological Evaluation of Oleanolic Acid Derivatives as Novel Inhibitors of Glycogen Phoshorylase" Bioorganic & Medicinal Chemistry Letters, vol. 16, No. (11), Mar. 20, 2006, pp. 2915-2919.

Huang, Tianming et al. "A Hydrophilic Conjugate Approach Toward the Design and Synthesis of Ursolic Acid Derivatives as Potential Antidiabetic Agent" RSC Adv., vol. 5, No. (55), May 11, 2015, pp. 44234-44246.

Lee, E.H et al. "Inhibitory Effect of Ursolic Acid Derivatives on Recombinant Human Aldose Reductase" Russian Journal of Bioorganic Chemistry, vol. 37, No. (5), Dec. 31, 2011, pp. 569-577.

Joshi, P. et al. "2-D QSAR Studies of Steroidal Natural Products Oleanic Acid and Their Semisynthetic Derivatives as Potent Protein Tyrosine Phosphatase 1B Inhibitors" Med Chem Res, vol. 21, No. (3), Jan. 7, 2011, pp. 351-361.

Hao, Jia et al. "Synthesis and Cytotoxicity Evaluation of Oleanolic Acid Derivatives" Bioorganic & Medicinal Chemistry Letters, vol. 23, No. (7), Feb. 8, 2013, pp. 2074-2077.

Zhong, Yan et al. "Synthesis, Stability and Pharmacological Evaluation of a Novel Codrug Consisting of Lamivudine and Ursolic Acid" European Journal of Pharmaceutical Sciences, vol. 45, No. 1-2, Nov. 9, 2011, pp. 110-115.

Parra, A. et al. "Solid-Phase Library Synthesis of Bi-Functional Derivatives of Oleanolic and Maslinic Acids and Their Cytotoxicity on Three Cancer Cells Lines" Comb. Sci., vol. 26, No. (8), Jun. 11, 2014. pp. 428-447.

Tian, Tian et al. "Synthesis of Novel Oleanolic Acid and Ursolic Acid in C-28 Position Derivatives as Potential Anticancer Agents" Arch. Pharm. Res., vol. 40, No. (4), Jan. 18, 2017, pp. 458-468.

Ma, Chaomei et al. "Chemical Modification of Oleanene Type Triterpenes and Their Inhibitory Activity Against HIV-1 Protease Dimerization" Chem. Pharm. Bull., vol. 48, No. (11), Nov. 30, 2000, pp. 1681-1688.

* cited by examiner

PENTACYCLIC TRITERPENE COMPOUND AND PREPARATION METHOD THEREFOR, AND PHARMACEUTICAL COMPOSITION AND USE THEREOF

CROSS-REFERENCE TO RELATED APPLICATIONS

This application is a national stage filing under 35 U.S.C. § 371 of International Application No. PCT/CN2018/106012, filed Sep. 17, 2018, which claims priority to Chinese Application No. 201710841681.8, filed Sep. 18, 2017, the entire contents of each which are incorporated herein by reference.

TECHNICAL FIELD

The present invention relates to a class of FXR antagonists, in particular, to a class of pentacyclic triterpene compounds, a method for preparing the same, and a pharmaceutical composition containing the compound, use in the preparation of FXR antagonist, and use in the preparation of a medicament for the treatment of cholestasis, hyperlipidemia, and diabetes.

BACKGROUND TECHNIQUE

The farnesoid X receptor (FXR) is a member of the nuclear receptor superfamily and is highly expressed in the liver, intestine, kidney, adrenal gland and adipose tissue. As a main regulator for endogenous bile acids, FXR receptor plays a key role in bile acid synthesis and enterohepatic circulation. FXR can regulate the levels of triglycerides, low-density lipoproteins, high-density lipoproteins, and blood glucose in the body through the complex regulatory network of the enterohepatic metabolic axis. In addition, FXR is also involved in processes such as liver injury and inflammation, liver cancer, and regulation of intestinal flora.

Because FXR is involved in many metabolic diseases, such as bile acid metabolism disorder, lipid metabolism disorder, and abnormal glucose metabolism, FXR modulators are expected to develop into medicament for a series of metabolic diseases such as cholestasis, hyperlipidemia, and diabetes. For example, obeticholic acid, a potent FXR agonist, has been successful in the Phase III clinical treatment of primary biliary cirrhosis and has been approved for marketing. In addition, obeticholic acid is undergoing a clinical research in diabetes with non-alcoholic liver (NASH) indications. There are also many reports of FXR antagonists, and some compounds have shown some effects in lowering blood lipids, lowering blood glucose or improving bile acid accumulation in pharmacodynamic experiments in vivo. Studies have shown that gut-specific FXR gene knockout mice are less susceptible to obesity and insulin resistance, and the team has found a bile acid derivative T-β-MCA that can antagonize FXR receptor, which is related to a series of improved metabolic functions, but the compound is rapidly degraded by the bile salt hydrolase BSH secreted by intestinal bacteria. Recently, a bile acid derivative, Gly-MCA, has been reported in the literature. It can selectively shut down FXR receptor in the intestine, prevent and reverse fatty liver in mice, and increase the sensitivity to insulin and blood glucose in mice fed with high-fat diets, and will not be degraded by BSH. It can be seen that the development of FXR antagonists may provide new ideas for the treatment of certain metabolic diseases, such as obesity, hyperlipidemia, type II diabetes, fatty liver and the like.

The FXR antagonists reported up to present mainly include two categories, natural product antagonists and synthetic small molecule antagonists. The natural product guggulsterone (GS) is the first reported FXR antagonist, but its selectivity is poor and it has effects on various nuclear receptors. The plant sterol stigmasterol acetate discovered by Carter et al. in 2007 and a series of marine natural products tuberatolides reported by Choi in 2011 can antagonize FXR, but due to the limited natural sources of the compounds and the difficulty of full synthesis, the structural optimization of such compounds has not been reported. The first non-steroidal FXR small molecule antagonist was reported by Kainuma's group in 2007, and was modified from the FXR agonist GW4064. Another class of representative small molecule antagonists are pyrazolone compounds discovered by Li Jian's group in 2012, which can dose-dependently reduce the levels of triglycerides and total cholesterol in pharmacodynamic experiments in cholesterol-fed mice. Whether a natural product or a synthetic small-molecule FXR antagonist, they generally have shortcomings such as weak activities and fewer types. Most of them are natural products with complex structures, so that it is difficult for subsequent development.

At present, there are few reports on pentacyclic triterpene compounds useful as FXR antagonists. The first reported pentacyclic triterpenoid FXR antagonist is platycodin D. It is later found that oleanolic acid also has weak FXR antagonistic activity. Recently, Fang Weishuo's group used oleanolic acid as a starting material to synthesize a class of 3-beta-oleanolic acid derivatives, and its FXR antagonistic activity has been improved. However, no report on betulinic acid derivatives useful as FXR antagonists has been reported.

SUMMARY OF THE INVENTION

An object of the present invention is to provide a pentacyclic triterpene compound useful as a farnesoid X receptor (FXR) antagonist.

In the first aspect of the present invention, it provides a compound represented by formula I or a pharmaceutically acceptable salt thereof:

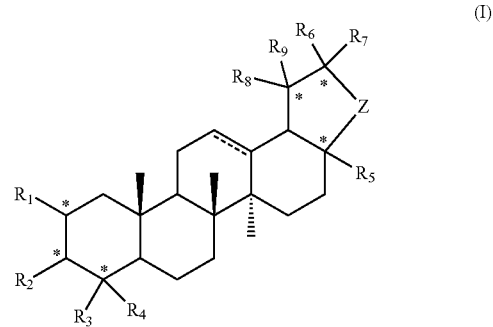

$R_1$ is hydrogen, hydroxyl, halogen or $C_1$-$C_6$ alkyl;
$R_2$ is hydrogen, hydroxyl, halogen, $C_1$-$C_6$ alkoxy, 3-10 membered cycloalkyloxy, =O, =N—OH, R—C(=O)—O—; where R is a substituted or unsubstituted following group: $C_1$-$C_8$ alkyl, $C_3$-$C_{10}$ cycloalkyl, $C_6$-$C_{10}$ aryl, 5-7 membered heteroaryl, $R_a$NH— or $R_a$O—; wherein each $R_a$ is independently selected from the group consisting of $C_1$-$C_8$ alkyl, $C_3$-$C_{10}$ cycloalkyl, $C_6$-$C_{10}$ aryl and 5-7 membered heteroaryl;

$R_3$ and $R_4$ are each independently unsubstituted or substituted $C_1$-$C_6$ alkyl;

$R_5$ is hydrogen, hydroxy, hydroxymethyl, formyl, or

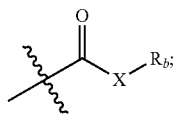

wherein X is NH, O or S, and $R_b$ is hydrogen, unsubstituted or substituted $C_1$-$C_6$ alkyl;

$R_6$, $R_7$, $R_8$ and $R_9$ are each independently hydrogen, hydroxyl or $C_1$-$C_6$ alkyl; Z is —$(CH_2)_n$—, n is 1, 2 or 3;

---- represents single or double bond;

each * independently represents R configuration, S configuration, or racemate;

the "substituted" means that the hydrogen on the group is substituted with one or more substituents selected from the group consisting of hydroxyl, halogen, $C_1$-$C_6$ alkyl, $C_1$-$C_6$ alkoxy, carboxyl (—COOH), and sulfo group (—$SO_2$OH).

In another preferred embodiment, $R_1$ is hydrogen or hydroxyl.

In another preferred embodiment, $R_1$ is hydrogen.

In another preferred embodiment, $R_2$ is hydroxyl or R—C(=O)—O—; where R is a substituted or unsubstituted following group: $C_1$-$C_6$ alkyl, $C_3$-$C_8$ cycloalkyl, $C_6$-$C_{10}$ aryl, 5-7 membered heteroaryl, $R_a$NH— or $R_a$O—; wherein each $R_a$ is $C_1$-$C_6$ alkyl;

the "substituted" means that the hydrogen on the group is substituted with one or more substituents selected from the group consisting of halogen, $C_1$-$C_6$ alkyl, and $C_1$-$C_6$ alkoxy.

In another preferred embodiment, $R_2$ is connected to the ring in α configuration.

In another preferred embodiment, $R_3$ and $R_4$ are each independently $C_1$-$C_4$ alkyl.

In another preferred embodiment, $R_3$ and $R_4$ are both methyl.

In another preferred embodiment, $R_5$ is hydroxymethyl, formyl, or

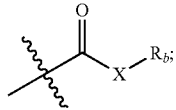

wherein X is NH or O, $R_b$ is hydrogen, or unsubstituted or substituted $C_1$-$C_4$ alkyl;

the "substituted" means that the hydrogen on the group is substituted with one or more substituents selected from the group consisting of $C_1$-$C_4$ alkyl, carboxyl (—COOH), and sulfo group (—$SO_2$OH).

In another preferred embodiment, $R_5$ is

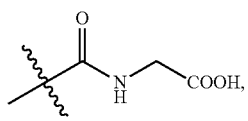 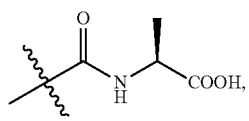

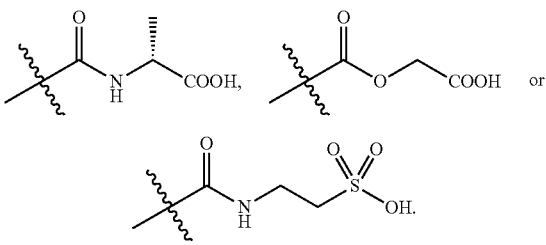

In another preferred embodiment, $R_6$ and $R_7$ are each independently hydrogen, methyl or ethyl;

$R_8$ and $R_9$ are each independently hydrogen, methyl, ethyl, n-propyl, isopropyl, n-butyl, tert-butyl or isobutyl.

In another preferred embodiment, the compound is:

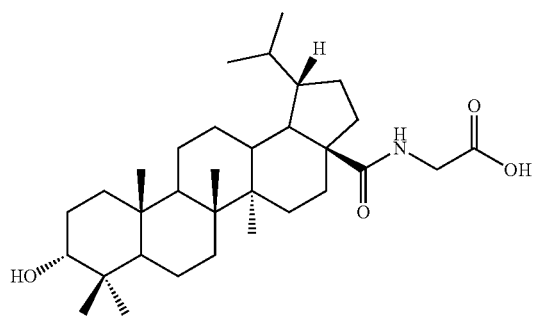

C1

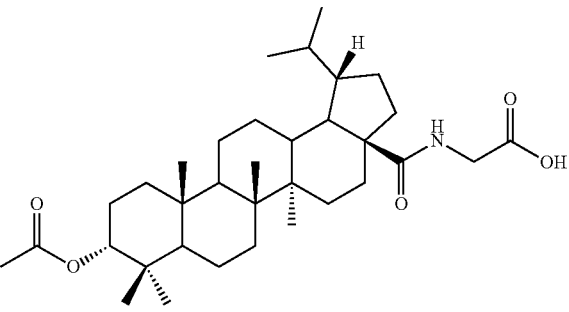

C2

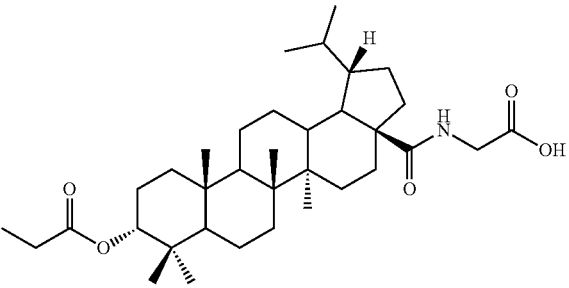

C3

C4
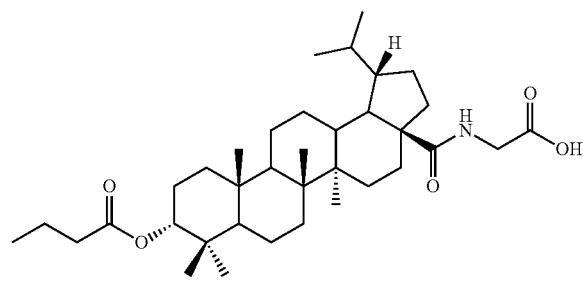
C5
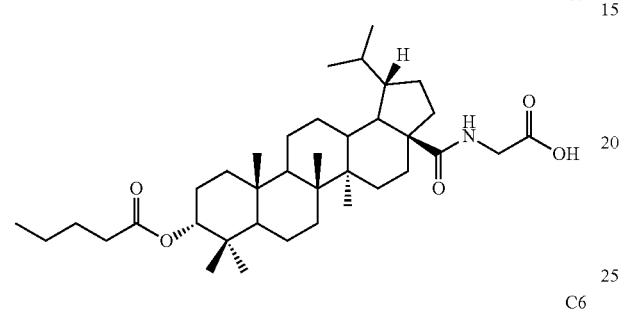
C6
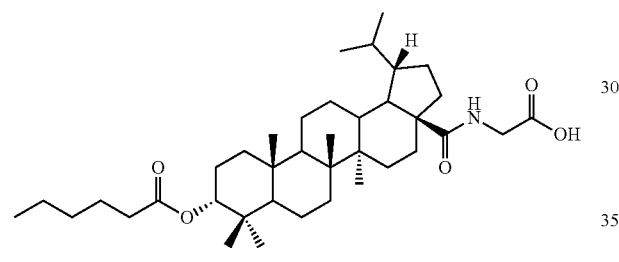
C7
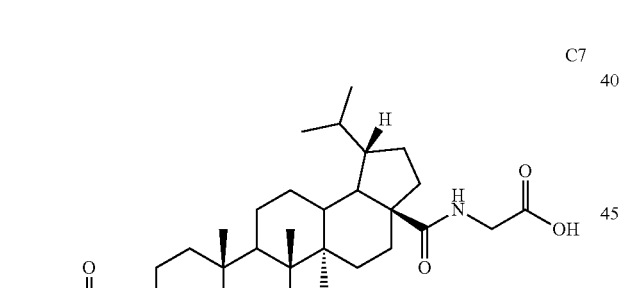
C8
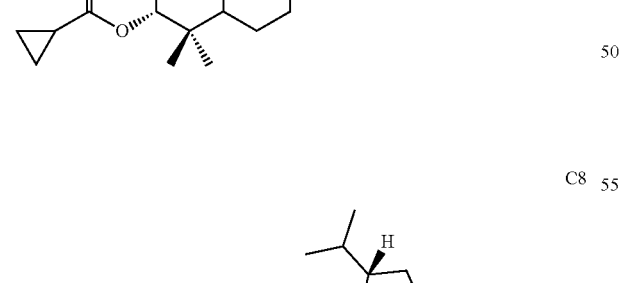
C9
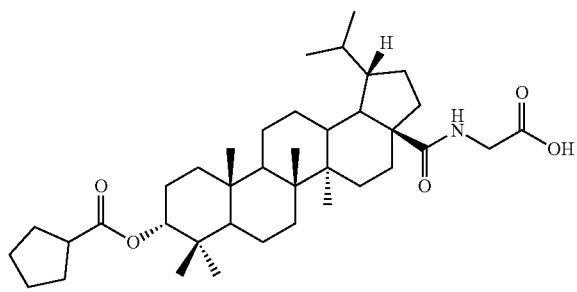
C10
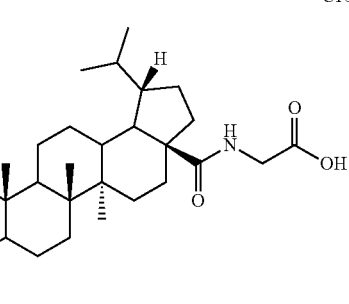
C11
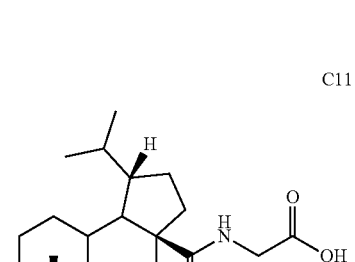
C12
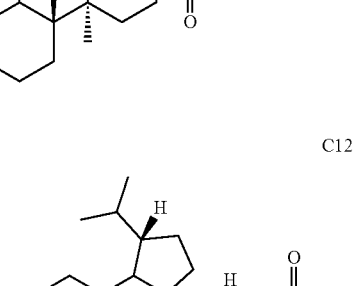
C13
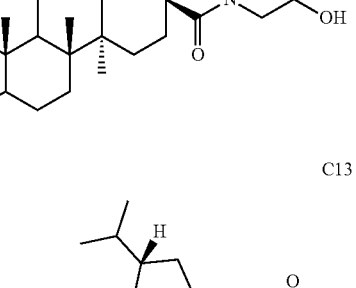

C14
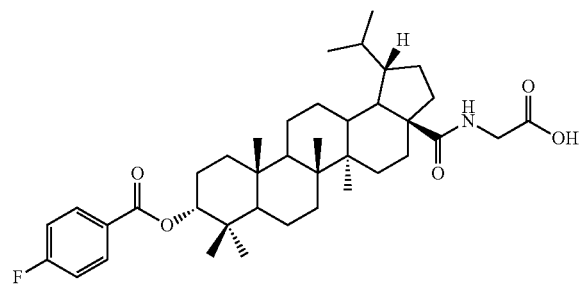
C19
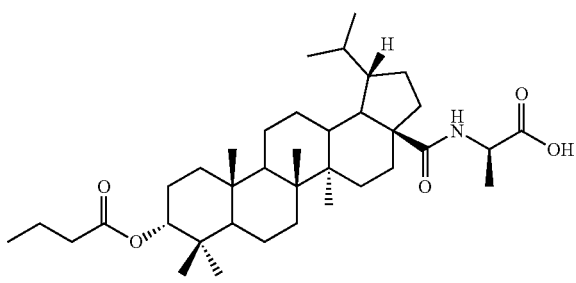
C15
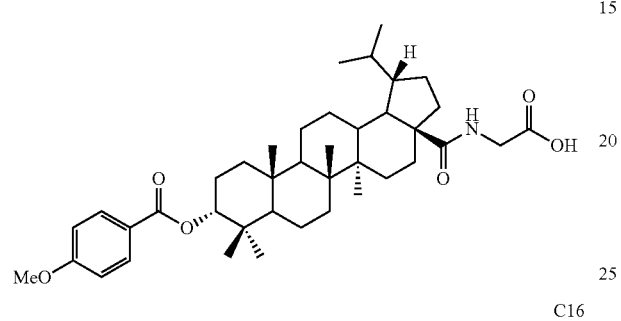
C20
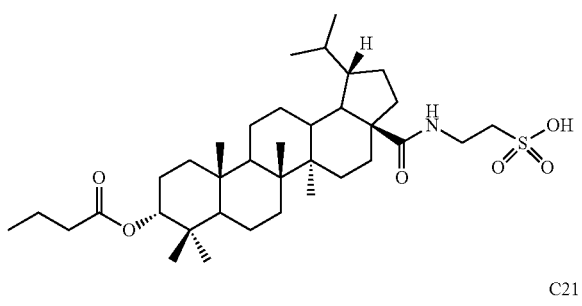
C16
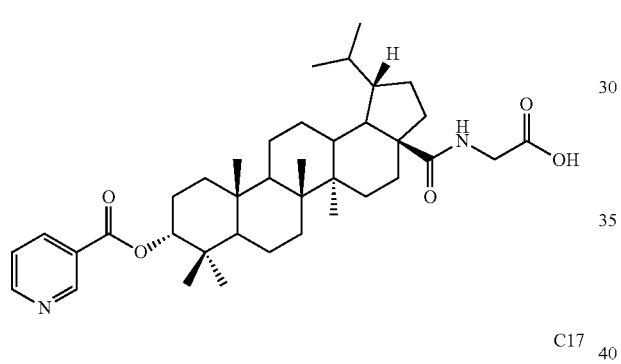
C21
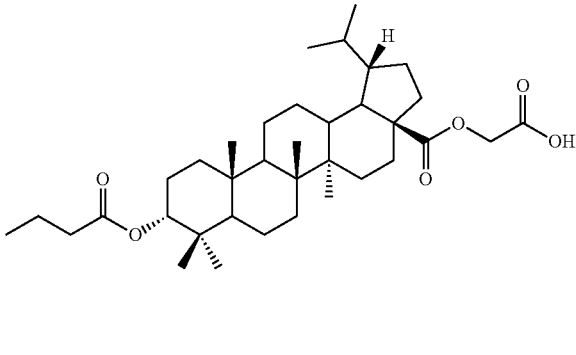
C17
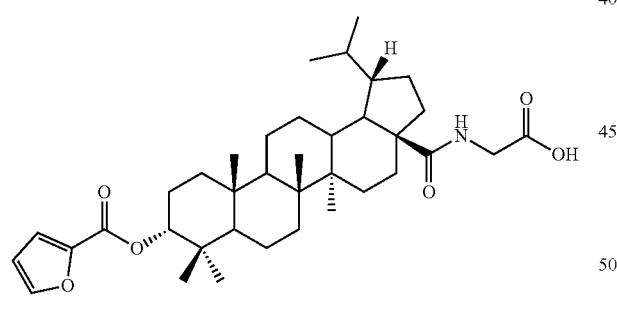
C22
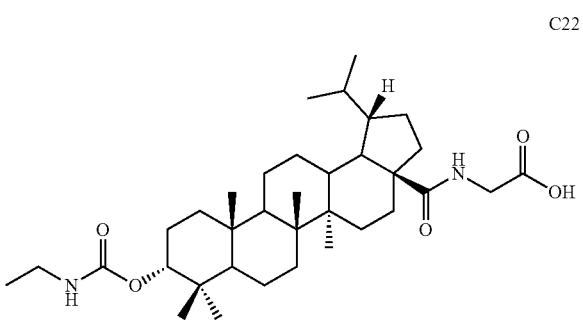
C18
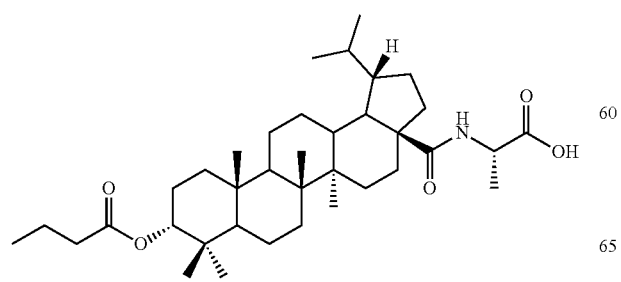
C23
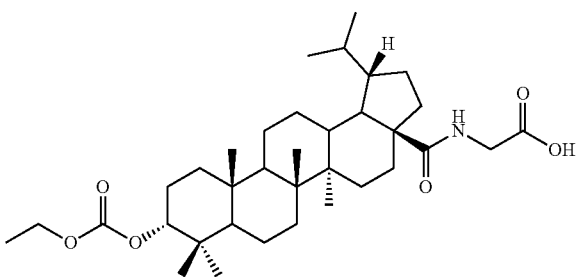

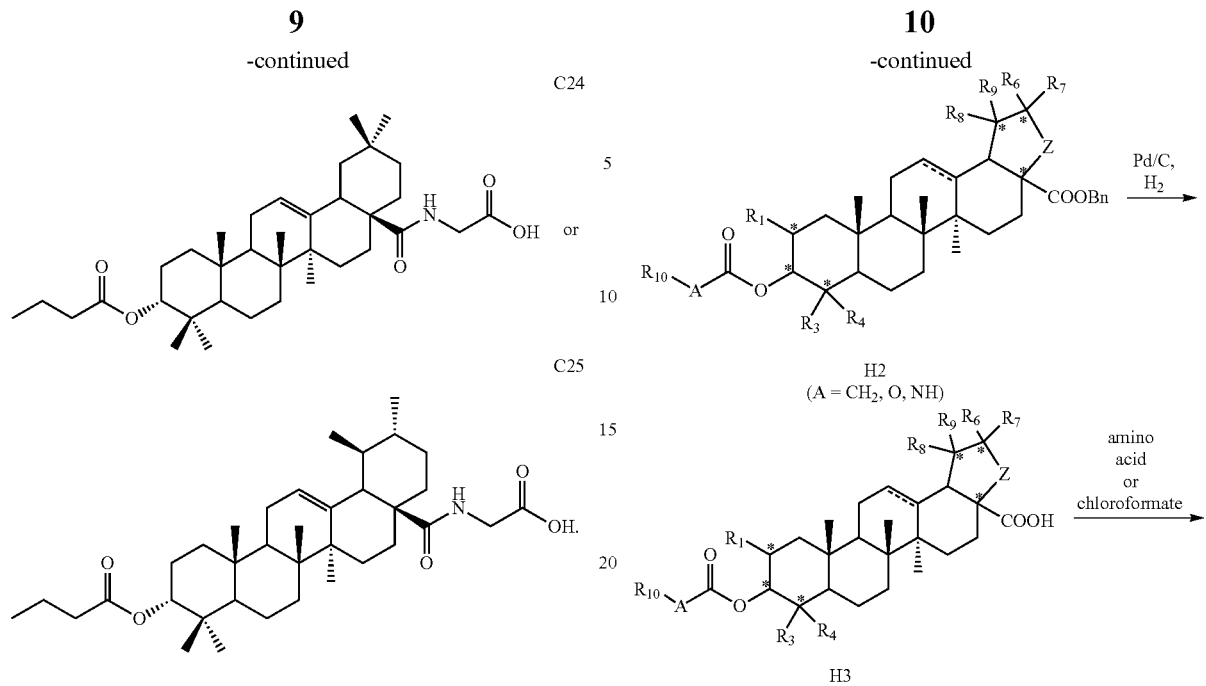

C24

C25

In the second aspect of the preset invention, it provides a method for preparing the compound or pharmaceutically acceptable salt thereof according to the first aspect, wherein

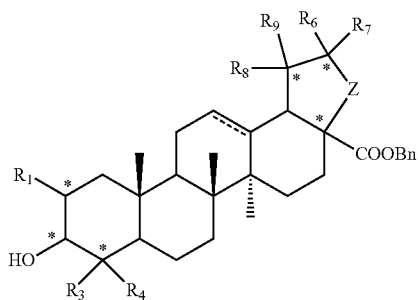

is used as a raw material and the compound according to the first aspect is obtained by introducing an ester group into hydroxyl at position 3, the benzyl protecting group is removed from carboxyl at position 17 by hydrogenation and then an amino acid group is introduced into carboxyl, wherein each substituent is defined as described in the first aspect.

In a preferred embodiment, the compound or pharmaceutically acceptable salt thereof is prepared by the following route:

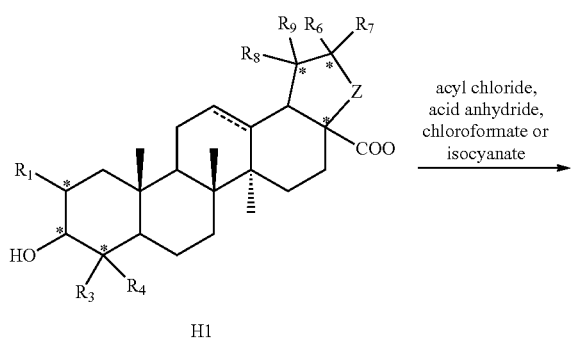

H1

H2
(A = CH$_2$, O, NH)

H3

H4
(B = O, NH)

reacting a compound of formula H1 with an acyl chloride, acid anhydride, chloroformate or isocyanate to obtain a compound of formula H2;

removing benzyl protecting group from the compound of formula H2 to obtain a compound of formula H3;

reacting a compound of formula H3 with an amino acid or chloroformate to obtain a compound of formula H4;

wherein, $R_{10}$ is a substituted or unsubstituted following group: $C_1$-$C_8$ alkyl, $C_3$-$C_{10}$ cycloalkyl, $C_6$-$C_{10}$ aryl, 5-7 membered heteroaryl, $R_a$NH— or $R_a$O—; wherein, each $R_a$ is independently selected from the group consisting of $C_1$-$C_8$ alkyl, $C_3$-$C_{10}$ cycloalkyl, $C_6$-$C_{10}$ aryl, 5-7 membered heteroaryl; $R_{11}$ is hydrogen, or unsubstituted or substituted $C_1$-$C_6$ alkyl.

The definition of substitution is the same as above.

In the third aspect of the present invention, it provides a pharmaceutical composition comprising the compound or pharmaceutically acceptable salt thereof according to the first aspect; and a pharmaceutically acceptable carrier.

In the fourth aspect of the present invention, it provides use of the compound or pharmaceutically acceptable salt thereof according to the first aspect or the use of a pharmaceutical composition according to the third aspect, (i) for the manufacture of a farnesoid X receptor (FXR) antagonist; or (ii) for the manufacture of a medicament for the treatment of a metabolic disease.

In another preferred example, the metabolic disease is selected from the group consisting of: hyperlipidemia, bile acid accumulation, diabetes, obesity, non-alcoholic fatty liver, and biliary cirrhosis.

A method for treating hyperlipidemia, characterized in that the method comprises administering the compound or pharmaceutically acceptable salt thereof according to the first aspect, or the pharmaceutical composition according to the third aspect to a subject in need.

The novel pentacyclic triterpenoids of the present invention can effectively antagonize FXR receptors, can antagonize FXR receptors at micromolar concentrations and has no agonistic effect on TGR5 receptor. Compared with some existing natural-derived FXR antagonists, it has richer natural sources and simpler synthetic methods.

It should be understood that, within the scope of the present invention, the above technical features of the present invention and the technical features specifically described in the following descriptions (such as the examples) can be combined with each other to form a new or preferred technical solution. Each feature disclosed in the description may be replaced by any alternative feature serving the same, equivalent, or similar purpose. Due to space limitations, they will not be repeated herein.

DETAILED DESCRIPTION

After extensive and intensive research, the inventors of the present application have developed a class of pentacyclic triterpenoids for the first time. The main feature is the inversion of the hydroxyl group at position 3 and the introduction of groups such as glycine or taurine into the carboxyl group at position 17. FXR antagonistic activity is significantly increased. The inventors studied the effect of this structure on the activity for the first time, and obtained a series of compounds with excellent performance. Compared with some existing natural-derived FXR antagonists, they have more abundant sources and can be synthetized simply. The compounds are expected to be novel medicaments acting on this target for treating metabolic diseases. Based on this, the present invention has been completed.

Terms

As used herein, the alkyl is preferably an aliphatic alkyl, which may be a linear or branched alkyl, and includes but is not limited to: methyl, ethyl, n-propyl, isopropyl, n-butyl, isobutyl, tert-butyl, etc. The expressions of the form "C1-C8" are intended to include those corresponding groups having 1, 2, 3, 4, 5, 6, 7, or 8 carbon atoms, for example, "C1-C8 alkyl" refers to an alkyl having 1, 2, 3, 4, 5, 6, 7, or 8 carbon atoms, and "C2-C10 alkenyl" refers to an alkenyl having 2, 3, 4, 5, 6, 7, 8, 9 or 10 carbon atoms.

As used herein, the alkenyl is preferably vinyl, propenyl, butenyl, styryl, phenylpropenyl or the like.

As used herein, halogen preferably refers to fluorine, chlorine, bromine or iodine.

As used herein, alkoxy refers to —O-(alkyl), wherein alkyl is as defined above. "$C_{1-6}$ alkoxy" refers to an alkyloxy group containing 1 to 6 carbons. Non-limiting examples include methoxy, ethoxy, propoxy, butoxy, and the like.

As used herein, the cycloalkyl may be a saturated or partially unsaturated monocyclic or polycyclic cyclic hydrocarbon substituent, including 3 to 20 carbon atoms, preferably 3 to 12 carbon atoms, and more preferably 3 to 10 carbon atoms. Non-limiting examples of monocyclic cycloalkyl include cyclopropyl, cyclobutyl, cyclopentenyl, cyclohexyl, cyclooctyl, and the like; and polycyclic cycloalkyl includes spiro, fused and bridged cycloalkyl.

As used herein, cycloalkyloxy refers to —O-(cycloalkyl), wherein cycloalkyl is as defined above.

The aryl refers to a 6 to 10 membered full-carbon monocyclic or fused polycyclic (that is, a ring sharing an adjacent carbon atoms pair) group, and the group has a conjugated π-electron system, such as phenyl and naphthyl. The aryl ring may be fused with heterocyclyl, heteroaryl, or cycloalkyl. Non-limiting examples include benzimidazole, benzothiazole, benzoxazole, benzoisoxazole, benzopyrazole, quinoline, benzoindole, benzodihydrofuran.

The heteroaryl refers to a heteroaromatic system containing 1 to 4 heteroatoms and 5 to 14 ring atoms, wherein the heteroatoms include oxygen, sulfur, and nitrogen. Heteroaryl is preferably 5- or 6-membered, such as furyl, thienyl, pyridyl, pyrrolyl, N-alkylpyrrolyl, pyrimidinyl, pyrazinyl, imidazolyl, tetrazolyl, and the like. The heteroaryl may be fused to an aryl, heterocyclyl or cycloalkyl, wherein the ring connected to the parent structure is a heteroaryl ring.

In the present invention, unless otherwise indicated,

indicates a connection site.

Unless otherwise specified, the structure formula described herein are intended to include all tautomeric, optical, and stereoisomeric forms (e.g., enantiomers, diastereomers, geometric isomers, or conformers). For example, R and S configurations containing asymmetric centers, (Z), (E) isomers of double bonds and conformational isomers of (Z), (E). The individual stereochemical isomers, tautomers or enantiomers, diastereomers or geometric isomers or tautomers, or a mixture of conformers of the compounds of the invention belong to the scope of the present invention.

The term "tautomers" means that structural isomers with different energies can exceed low energy barriers and thus be converted into each other. For example, proton tautomers (i.e., proton shifts) include interconversions via proton migration, such as 1H-indazole and 2H-indazole, 1H-benzo[d]imidazole and 3H-benzo[d]imidazole. The valence tautomers include interconversions by reorganization of some bonding electrons.

The pharmaceutically acceptable salts herein are not particularly limited, and preferably include: inorganic acid salts, organic acid salts, alkyl sulfonates, and aryl sulfonates; the inorganic acid salts include hydrochloride, hydrobromide, nitrate, sulfate, phosphate, etc.; the organic acid salts include formate, acetate, propionate, benzoate, maleate, fumarate, succinate, tartrate, citrate, etc.; the alkyl sulfonates include methyl sulfonate, ethyl sulfonate, etc.; and the aryl sulfonates include benzenesulfonate, p-toluenesulfonate, and the like.

Preparation Method
The pentacyclic triterpene compounds of the present invention can be prepared by the following route.
Route 1:
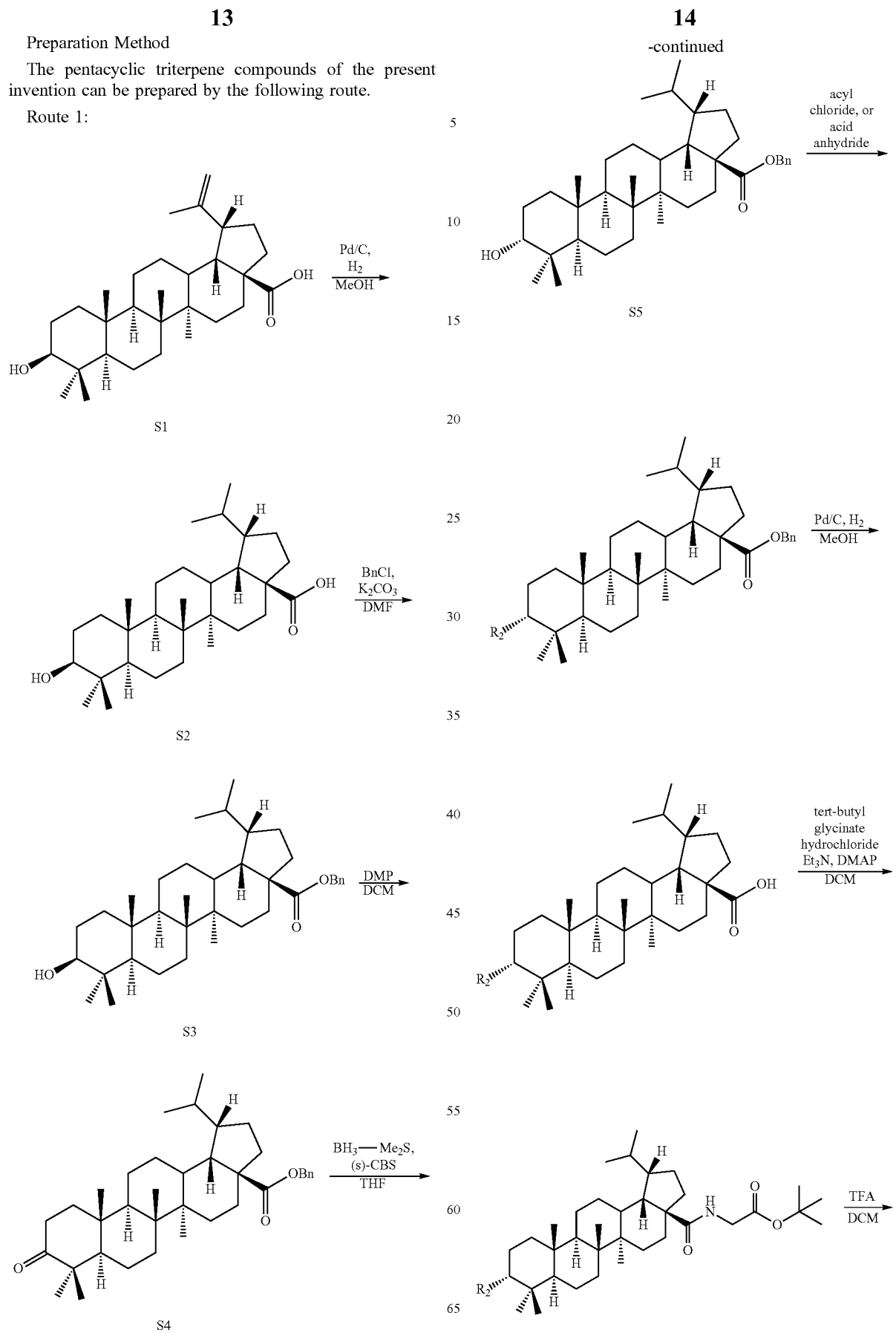

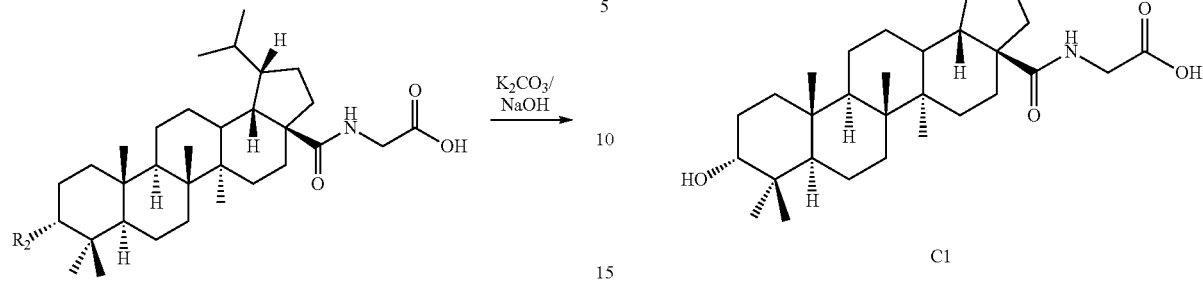
Route 2:
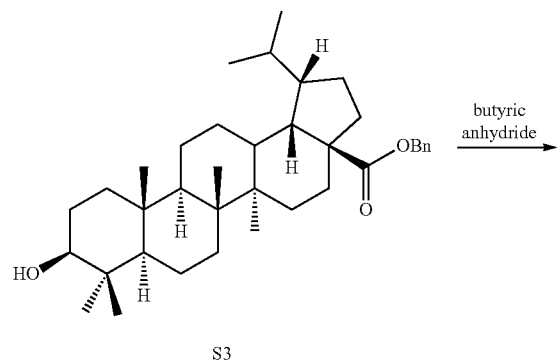
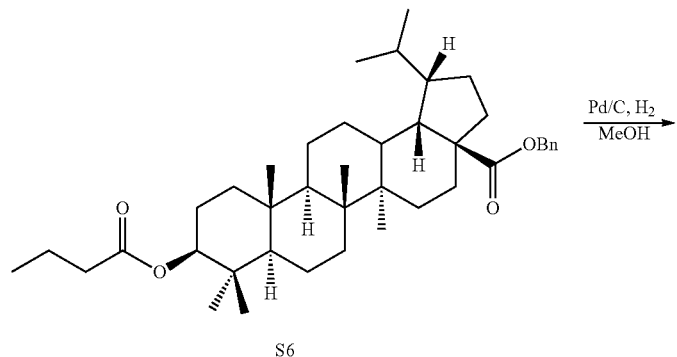
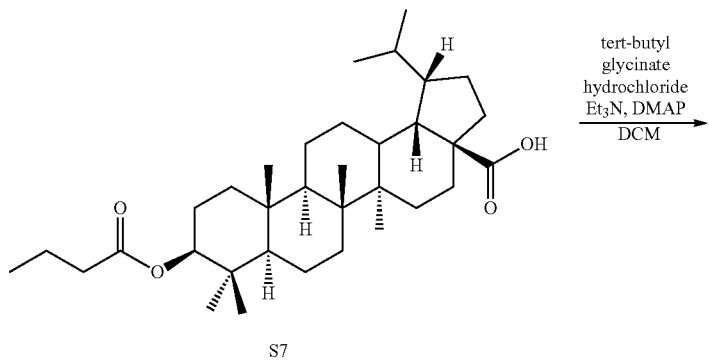

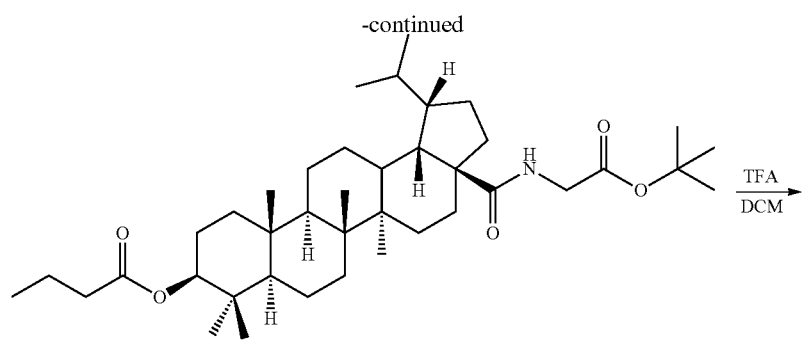
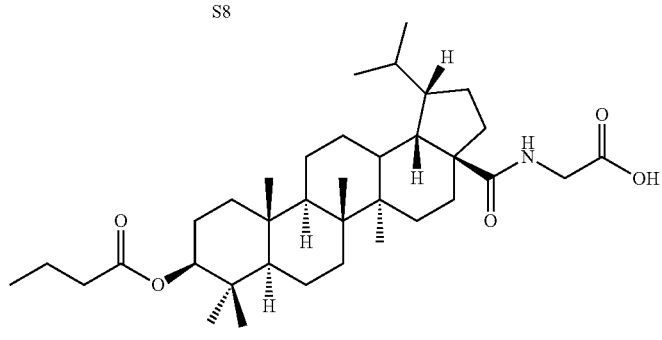
Route 3:

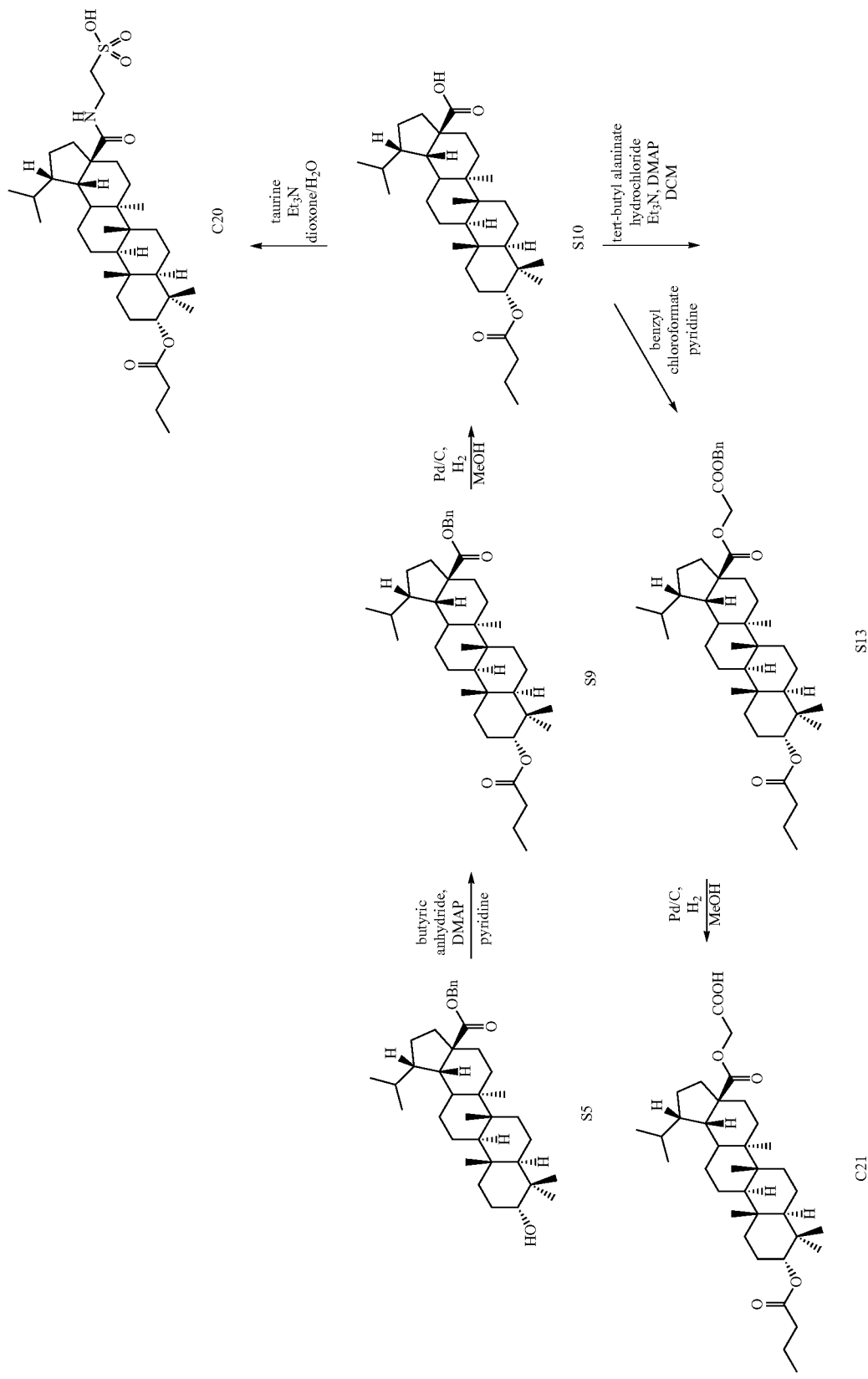

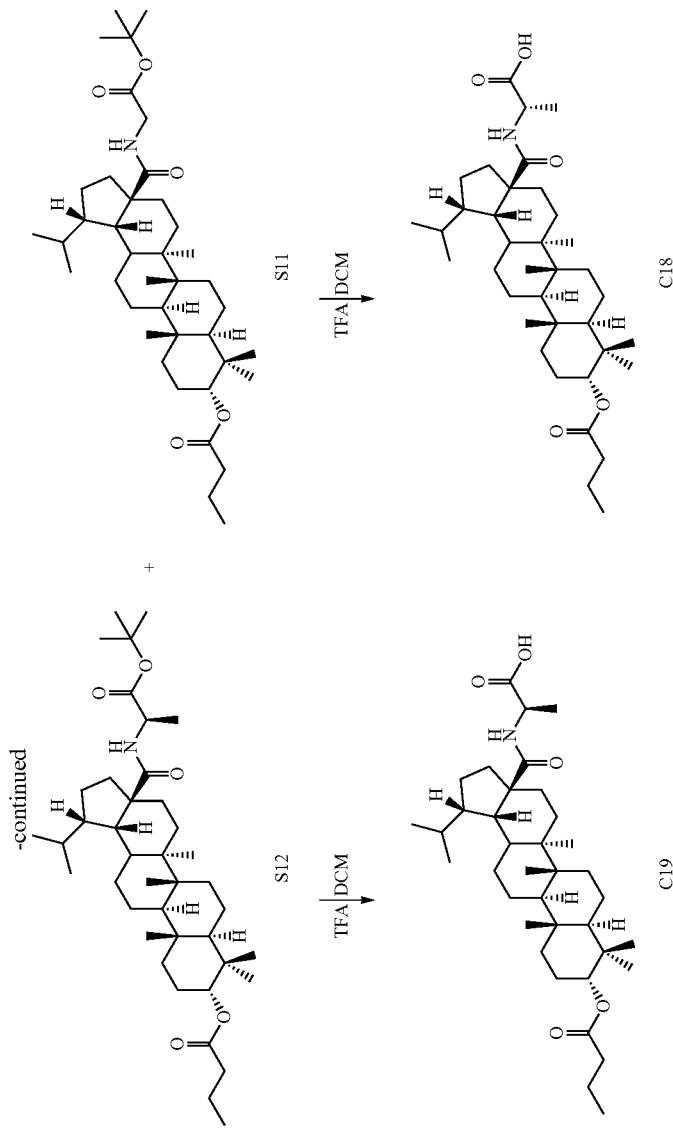

Route 4:

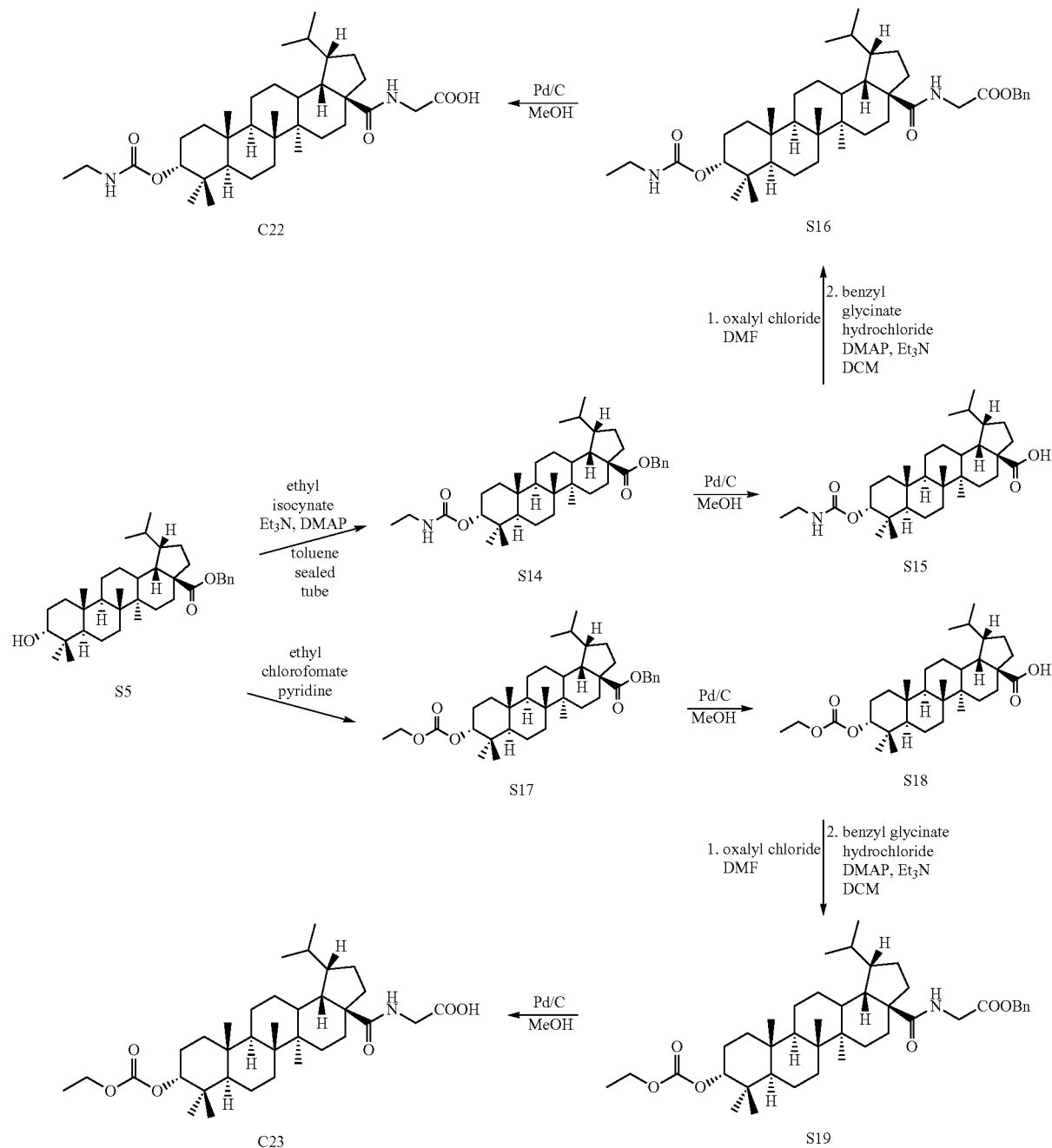

The present invention is further described below with reference to specific examples. It should be understood that these examples are only used to illustrate the present invention and not to limit the scope of the present invention. The experimental methods without specific conditions in the following examples are usually performed according to conventional conditions (such as those described in Sambrook et al., Molecular Cloning: Laboratory Manual (New York: Cold Spring Harbor Laboratory Press, 1989)) or according to conditions recommended by the manufacturer. Unless stated otherwise, percentage and part are percentage by weight and part by weight.

Unless otherwise defined, all professional and scientific terms used in this application have the same meanings as those familiar to those skilled in the art. In addition, any methods and materials similar or equal to the contents described can be used in the method of the present invention. The preferred methods and materials described herein are for demonstration purposes only.

In the following preparation examples, NMR was measured with a Mercury-Vx 300M instrument manufactured by Varian, and the NMR was calibrated: δ H 7.26 ppm (CDCl$_3$), 2.50 ppm (DMSO-d$_6$); MS was measured with Agilent 1200 Quadrupole LC/MS instrument or SHIMADZU GCMS- QP5050A; reagents were mainly provided by Shanghai Chemical Reagent Company; the silica gel plate used in TLC thin-layer chromatography was produced by Shandong Yantai Huiyou Silica Gel Development Co., Ltd. (model HSGF 254); and the normal phase column chromatography silica gel used for compound purification was produced by branch plat of Shandong Qingdao Marine Chemical Plant (model zcx-11, 200-300 mesh).

The full term corresponding to the abbreviations in the application are as follows.

DMAP: 4-dimethylaminopyridine; DCM: dichloromethane; DMF: N,N-dimethylformamide; TFA: trifluoroacetic acid.

EXAMPLE 1

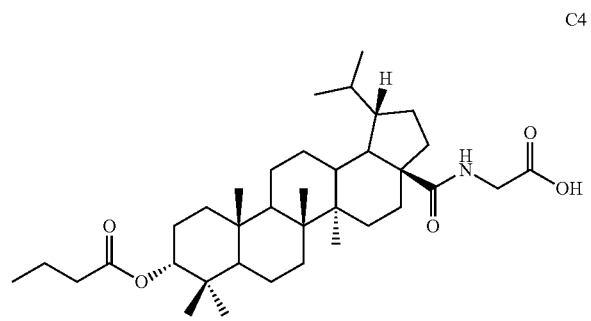

C4

(1) The raw material betulinic acid S1 (1.2 g, 2.63 mmol) was dissolved in methanol (50 mL) at room temperature. After the nitrogen was charged, 10% Pd/C was quickly added, then the nitrogen was charged and then hydrogen was charged. The mixture was stirred at room temperature. After 24 hours, TLC detection showed that the reaction was complete. After the nitrogen was charged, Pd/C was filtered off, and the reaction solution was dried by rotary evaporation and separated by column chromatography using an eluent system of petroleum ether/ethyl acetate (10:1) to obtain the compound S2 (1.04 g, 2.27 mmol) as a white solid in a molar yield of 86%. $^1$H NMR (300 MHz, CDCl$_3$) δ 3.13 (t, 1H, J=9.0, 6.9 Hz), 2.28-2.16 (m, 2H), 1.98-1.78 (m, 4H), 1.64-0.96 (m, other aliphatic ring protons), 0.96 (s, 3H), 0.93 (s, 3H), 0.92 (s, 3H), 0.90 (s, 3H), 0.89 (s, 3H), 0.87 (s, 3H), 0.78 (s, 3H).

(2) The product S2 (1.04 g, 2.27 mmol) was dissolved in DMF (20 mL) at room temperature, anhydrous potassium carbonate (0.626 g, 4.54 mmol) was added, and benzyl chloride (0.313 mL, 2.72 mmol) was slowly added dropwise with stirring. After the addition was complete, the reaction solution was stirred at 50° C. for 3 h. The reaction was monitored by TLC. After the reaction was complete, the mixture was cooled to room temperature, diluted with 50 mL of deionized water, and extracted with ethyl acetate (2×50 mL). The combined organic layers were washed separately with deionized water and saturated brine, dried over sodium sulfate, and distilled under reduced pressure to obtain the desired compound S3 (1.21 g, 2.20 mmol) as a white solid in a molar yield of 97%, which was directly used in the next reaction.

(3) S3 (1.21 g, 2.20 mmol) was dissolved in dichloromethane (30 mL) in an ice-water bath, and Dess-Martin oxidant (1.87 g, 4.40 mmol) was added in portions. The mixture was slowly warmed to room temperature and stirred for 1 hour. Then the reaction mixture was filtered and dried by rotary evaporation, and separated by column chromatography using an eluent system of petroleum ether/ethyl acetate (10:1) to obtain compound S4 (0.983 g, 1.80 mmol) as a white solid in a molar yield of 82%. $^1$H NMR (300 MHz, CDCl$_3$) δ 7.38-7.30 (m, 5H), 5.16-5.05 (m, 2H), 2.55-2.34 (m, 2H), 2.31-2.18 (m, 3H), 1.95-1.12 (m, other aliphatic ring protons), 1.06 (s, 3H), 1.01 (s, 3H), 0.93 (s, 3H), 0.91 (s, 3H), 0.86 (d, 3H, J=6.9 Hz), 0.79-0.73 (m, 6H).

(4) The product S4 (0.983 g, 1.80 mmol) and S-(-)-2-methyloxazoleborane (100 mg, 0.36 mmol) were loaded into a 100 mL dried round-bottomed flask and THF (70 mL) treated with fresh sodium wire was added. A 10 M solution of boranein tetrahydrofuran (0.32 mL) was slowly added dropwise at room temperature, wherein the drop rate was controlled and addition was completed within ten minutes. Then the mixture was stirred at room temperature for ten minutes. TLC monitoring showed that the reaction was complete. The reaction flask was moved to an ice-water bath, and methanol was slowly added to quench the reaction. After no more bubbles were formed, the solvent was removed by rotary evaporation. The residue was separated by column chromatography using an eluent system of petroleum ether/ethyl acetate (10:1) to obtain compound S5 (827 mg, 1.51 mmol) as a white solid in a molar yield of 84%. $^1$H NMR (300 MHz, CDCl$_3$) δ 7.37-7.30 (m, 5H), 5.15-5.06 (m, 2H), 3.38 (t, 1H, J=3.0 Hz), 2.55-2.34 (m, 2H), 2.31-2.18 (m, 3H), 1.95-1.12 (m, other aliphatic ring protons), 0.94 (s, 3H), 0.93 (s, 3H), 0.91 (s, 3H), 0.85-0.82 (m, 9H), 0.75-0.73 (m, 6H).

(5) Compound S5 (110 mg, 0.20 mmol) and a catalytic amount of DMAP (2.4 mg, 0.02 mmol) were dissolved in dichloromethane (5 mL) and triethylamine (83 μL, 0.60 mmol) was added. Butyric anhydride (98 μL, 0.60 mmol) was added dropwise under an ice-water bath and the mixture was reacted at room temperature for 12 hours. TLC showed that the reaction was complete. After the solvent was removed by concentration, the residue was diluted with ethyl acetate. The organic phase was washed separately with water and saturated aqueous sodium chloride solution, dried and concentrated over anhydrous sodium sulfate, and separated by column chromatography using an eluent system of petroleum ether/ethyl acetate (10:1) to obtain product S9 (111 mg, 0.18 mmol) in a molar yield of 90%. $^1$H NMR (300 MHz, CDCl$_3$) δ 7.38-7.30 (m, 5H), 5.15-5.06 (m, 2H), 4.62 (t, 1H, J=3.0 Hz), 2.34-2.16 (m, 4H), 1.93-1.04 (m, other aliphatic ring protons), 0.97 (t, 6H, J=7.2 Hz), 0.87-0.86 (m, 3H), 0.84-0.82 (m, 6H), 0.76-0.73 (m, 6H).

(6) The product S9 (111 mg, 0.18 mmol) was dissolved in methanol (10 mL) and a small amount of ethyl acetate. After the nitrogen was charged, 10% Pd/C was quickly added, then the nitrogen was charged and then hydrogen was charged. The mixture was stirred at room temperature. After 1 hour, TLC detection showed that the reaction was complete. After the nitrogen was charged, 10% Pd/C was filtered off. The reaction solution was dried by rotary evaporation and then separated by column chromatography using an eluent system of petroleum ether/ethyl acetate (9:1) to obtain compound S10 (79 mg, 0.15 mmol) as a white solid in a molar yield of 83%. $^1$H NMR (300 MHz, CDCl$_3$) δ 4.61 (s, 1H), 2.30 (t, 2H, J=7.5 Hz), 2.28-2.15 (m, 4H), 1.98-1.15 (m, other aliphatic ring protons), 0.94 (s, 3H), 0.91 (s, 3H), 0.90 (t, 3H, J=6.0 Hz), 0.85 (s, 3H), 0.83 (s, 3H), 0.82 (s, 3H), 0.75 (s, 3H), 0.73 (s, 3H).

(7) The product S10 (79 mg, 0.15 mmol) and a catalytic amount of DMF (2 μL, 0.02 mmol) were dissolved in 2 mL dried dichloromethane, and oxalyl chloride (125 μL, 1.5 mmol) was added at 0° C. After 10 min, the mixture was warmed to room temperature and stirred for 3 hours. Dichloromethane was directly removed by rotary evaporation and the residue was dried with an oil pump and then used in next reaction. Tert-butyl glycinate hydrochloride (51 mg, 0.30 mmol) and a catalytic amount of DMAP (3.7 mg, 0.03 mmol) were dissolved in 1 mL dichloromethane and triethylamine (103 μL, 0.75 mmol) was added dropwise at 0° C. Then 1 mL freshly prepared solution of acyl chloride in dichloromethane was added dropwise. After 10 minutes, the mixture was warmed to room temperature and reacted at room temperature for 12 hours. TLC showed that the reaction was complete. The solvent was removed by concentration and then the residue was diluted with ethyl acetate. The organic phase was washed separately with water and aqueous saturated sodium chloride solution, dried and concentrated over anhydrous sodium sulfate, and separated by column chromatography using an eluent system of petroleum ether/ethyl acetate (8:1) to obtain the product (83 mg, 0.13 mmol) in a molar yield of 87%. $^1$H NMR (300 MHz, CDCl$_3$) δ 6.02 (t, 1H, J=5.1 Hz), 4.62 (t, 1H, J=3.0 Hz), 3.91-3.88 (m, 2H), 2.48-2.38 (m, 1H), 2.31 (t, 2H, J=7.5 Hz), 2.04-2.00 (m, 1H), 1.91-1.04 (m, other aliphatic ring protons), 1.47 (s, 9H), 1.04-0.95 (m, 6H), 0.92 (s, 3H), 0.86-0.82 (m, 12H), 0.74 (d, 3H, J=6.6 Hz).

(8) The product from previous step (83 mg, 0.13 mmol) was dissolved in 3 mL dichloromethane and 0.2 mL TFA was added. The mixture was stirred at room temperature for 1 hour, and TLC showed that the reaction was complete. The solvent was directly removed by rotary evaporation and the residue was separated by column chromatography using an eluent system of dichloromethane/methanol (20:1) to obtain the product C4 (59 mg, 0.10 mmol) in a molar yield of 77%. $^1$H NMR (300 MHz, CDCl$_3$) δ 6.16 (s, 1H), 4.63 (t, 1H, J=2.7 Hz), 4.07 (s, 2H), 2.41-2.21 (m, 4H), 2.05-1.04 (m, other aliphatic ring protons), 1.00-0.95 (m, 6H), 0.92 (s, 3H), 0.87-0.83 (m, 12H), 0.75 (d, 3H, J=6.9 Hz).

The following compounds were synthesized from different acid anhydrides or acyl chlorides by using the same preparation method as example 1.

| Compound | Structure | NMR |
| --- | --- | --- |
| C2 | 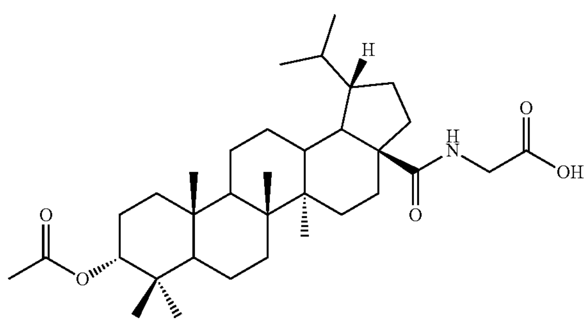 | $^1$H NMR (300 MHz, CDCl$_3$) δ 6.23-6.19 (m, 1H), 4.61 (s, 1H), 4.04 (d, 2H, J = 6.9 Hz), 2.42-2.33 (m, 1H), 2.31-2.23 (m, 1H), 2.07 (s, 3H), 2.02-1.05 (m, other aliphatic ring protons), 1.00 (s, 3H), 0.92 (s, 3H), 0.86-0.82 (m, 12H), 0.74 (d, 3H, J = 6.6 Hz). |
| C3 | 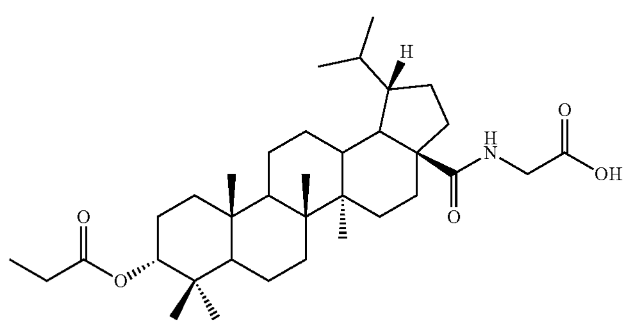 | $^1$H NMR (300 MHz, CDCl$_3$) δ 6.13-6.09 (m, 1H), 4.62 (s, 1H), 4.07-4.04 (m, 2H), 2.43-1.10 (m, other aliphatic ring protons), 1.00 (s, 3H), 0.93 (s, 3H), 0.87-0.83 (m, 12H), 0.75 (d, 3H, J = 6.3 Hz). |
| C5 | 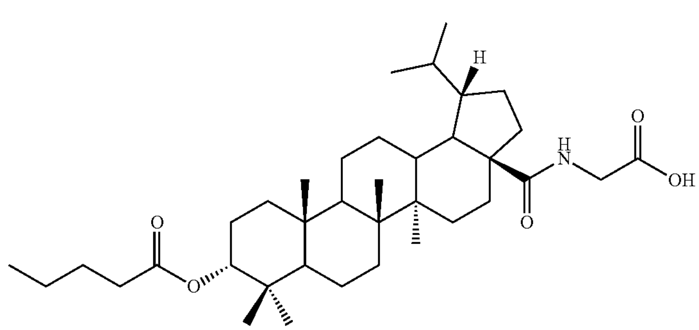 | $^1$H NMR (300 MHz, CDCl$_3$) δ 6.16-6.13 (m, 1H), 4.62 (t, 1H, J = 2.7 Hz), 4.06-4.04 (m, 2H), 2.43-2.23 (m, 3H), 2.04-1.04 (m, other aliphatic ring protons), 1.00 (s, 3H), 0.93-0.89 (m, 6H), 0.87-0.83 (m, 12H), 0.74 (d, 3H, J = 6.6 Hz). |

| Compound | Structure | NMR |
|---|---|---|
| C6 | 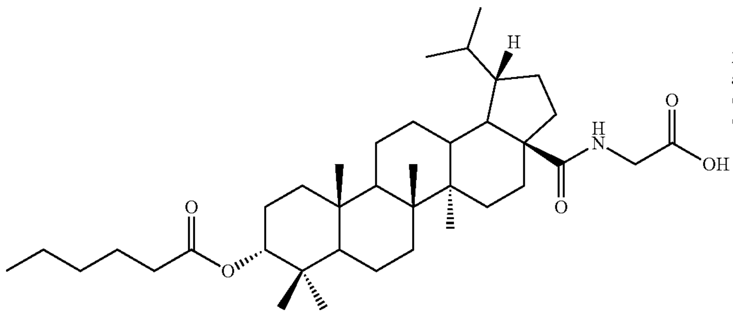 | $^1$H NMR (300 MHz, CDCl$_3$) δ 6.16-6.13 (m, 1H), 4.62 (t, 1H, J = 3.0 Hz), 4.06-4.04 (m, 2H), 2.43-2.40 (m, 4H), 2.04-1.04 (m, other aliphatic ring protons), 1.00 (s, 3H), 0.93-0.89 (m, 6H), 0.87-0.83 (m, 12H), 0.75 (d, 3H, J = 6.6 Hz). |
| C7 | 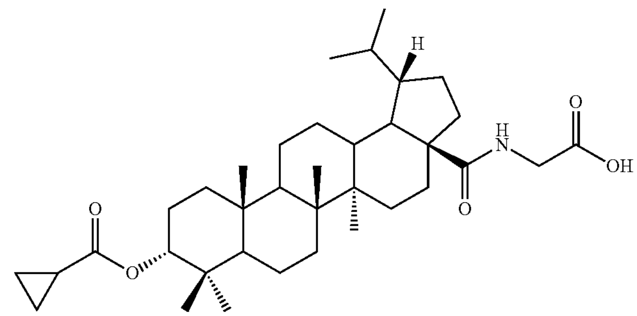 | $^1$H NMR (300 MHz, CDCl$_3$) δ 6.24 (t, 1H, J = 5.1 Hz), 4.61 (t, 1H, J = 2.4 Hz), 4.04 (d, 2H, J = 5.1 Hz), 2.43-2.34 (m, 1H), 2.30-2.22 (m, 1H), 2.10-2.02 (m, 1H), 1.91-1.07 (m, other aliphatic ring protons), 1.04-0.95 (m, 5H), 0.92 (s, 3H), 0.86-0.84 (m, 14H), 0.75 (d, 3H, J = 6.6 Hz). |
| C8 | 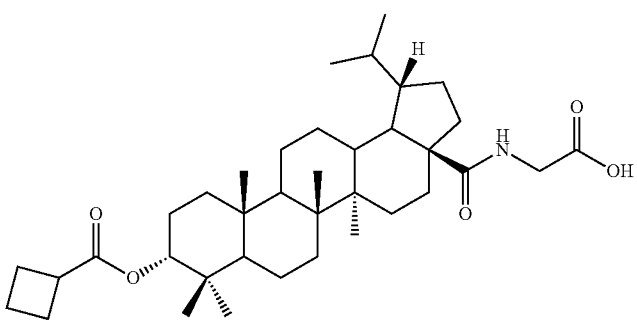 | $^1$H NMR (300 MHz, CDCl$_3$) δ 6.18-6.15 (m, 1H), 4.62-4.60 (m, 1H), 4.07-4.04 (m, 2H), 3.23-3.11 (m, 1H), 2.42-2.16 (m, 6H), 2.11-1.04 (m, other aliphatic ring protons), 0.99 (s, 3H), 0.92 (s, 3H), 0.87-0.83 (m, 12H), 0.75 (d, 3H, J = 6.6 Hz). |
| C9 | 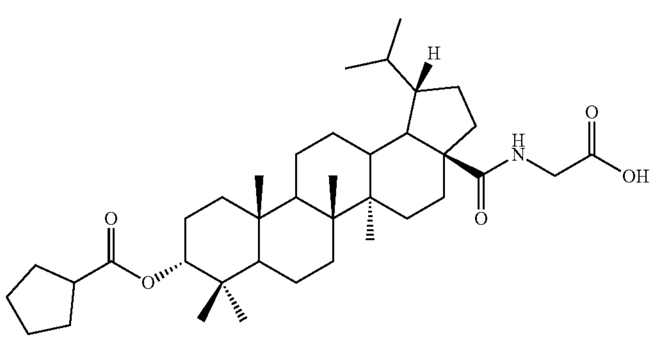 | $^1$H NMR (300 MHz, CDCl$_3$) δ 6.16-6.12 (m, 1H), 4.60-4.58 (m, 1H), 4.07-4.04 (m, 2H), 2.83-2.73 (m, 1H), 2.44-2.34 (m, 1H), 2.31-2.24 (m, 1H), 2.04-1.04 (m, other aliphatic ring protons), 0.99 (s, 3H), 0.93 (s, 3H), 0.87-0.83 (m, 12H), 0.75 (d, 3H, J = 6.6 Hz). |

| Compound | Structure | NMR |
|---|---|---|
| C10 | 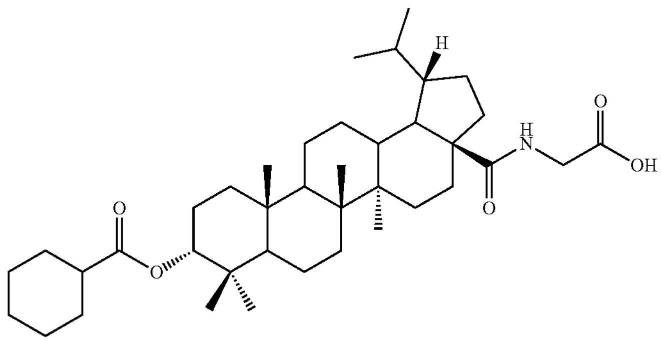 | $^1$H NMR (300 MHz, CDCl$_3$) δ 6.16-6.13 (m, 1H), 4.61-4.59 (m, 1H), 4.07-4.04 (m, 2H), 2.44-2.24 (m, 3H), 2.05-1.09 (m, other aliphatic ring protons), 1.00 (s, 3H), 0.93 (s, 3H), 0.88-0.83 (m, 12H), 0.75 (d, 3H, J = 6.9 Hz). |
| C11 | 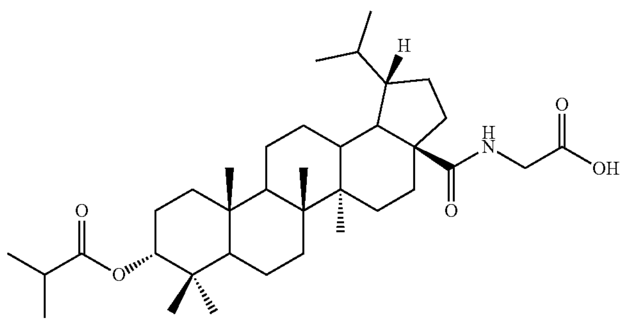 | $^1$H NMR (300 MHz, CDCl$_3$) δ 6.20 (t, 1H, J = 5.4 Hz), 4.59 (s, 1H), 4.06-4.04 (m, 2H), 2.63-2.53 (m, 1H), 2.43-2.21 (m, 2H), 2.13-1.04 (m, other aliphatic ring protons), 1.20 (d, 3H, J = 1.5 Hz), 1.17 (d, 3H, J = 1.2 Hz), 0.99 (s, 3H), 0.92 (s, 3H), 0.87-0.83 (m, 12H), 0.74 (d, 3H, J = 6.6 Hz). |
| C13 | 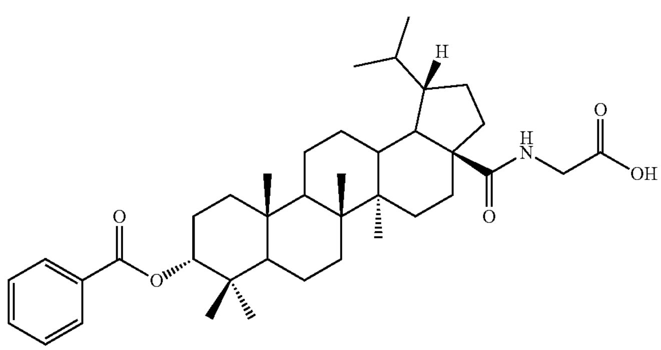 | $^1$H NMR (300 MHz, CDCl$_3$) δ 8.07-8.04 (m, 2H), 7.59-7.54 (m, 1H), 7.50-7.44 (m, 2H), 6.16-6.12 (m, 1H), 4.89 (s, 1H), 4.08-4.05 (m, 2H), 2.45-2.36 (m, 1H), 2.32-2.25 (m, 1H), 2.11-1.15 (m, other aliphatic ring protons), 1.04 (s, 3H), 0.96-0.95 (m, 6H), 0.92-0.91 (m, 6H), 0.86 (d, 3H, J = 6.9 Hz), 0.75 (d, 3H, J = 6.0 Hz) |
| C14 | 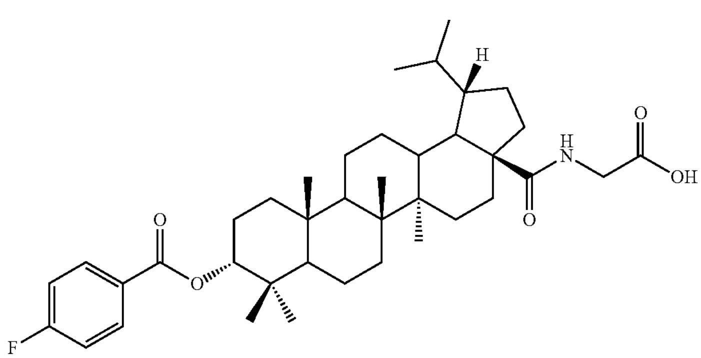 | $^1$H NMR (300 MHz, CDCl$_3$) δ 8.08-8.03 (m, 2H), 7.17-7.11 (m, 2H), 6.14-6.11 (m, 1H), 4.87 (s, 1H), 4.08-4.05 (m, 2H), 2.45-2.37 (m, 2H), 2.32-2.24 (m, 2H), 2.08-1.13 (m, other aliphatic ring protons), 1.13 (s, 3H), 0.96 (s, 3H), 0.95 (s, 3H), 0.91 (s, 6H), 0.86 (d, 3H, J = 6.9 Hz), 0.75 (d, 3H, J = 6.9 Hz). |

| Compound | Structure | NMR |
|---|---|---|
| C15 | 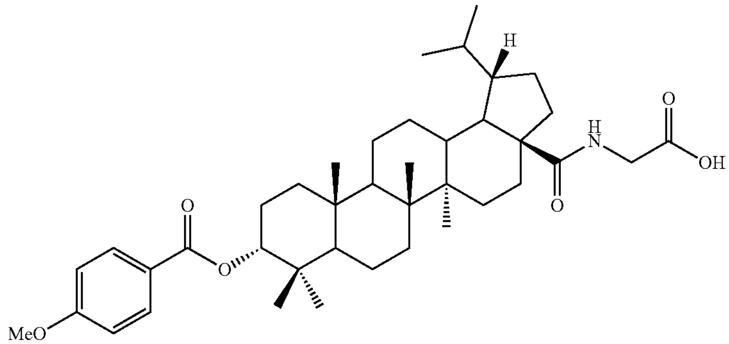 | ¹H NMR (300 MHz, CDCl₃) δ 8.01 (d, 2H, J = 8.7 Hz), 6.95 (d, 2H, J = 9.0 Hz), 6.15 (t, 1H, J = 5.4 Hz), 4.85 (t, 1H, J = 3.0 Hz), 4.08-4.05 (m, 2H), 3.87 (s, 3H), 2.44-2.36 (m, 1H), 2.31-2.24 (m, 1H), 2.11-1.16 (m, other aliphatic ring protons), 1.04 (s, 3H), 0.96 (s, 3H), 0.94 (s, 3H), 0.91-0.90 (m, 6H), 0.85 (d, 3H, J = 6.9 Hz), 0.75 (d, 3H, J = 6.6 Hz). |
| C16 | 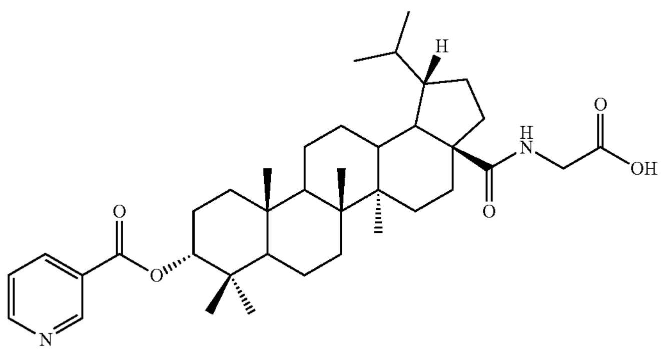 | ¹H NMR (300 MHz, CDCl₃) δ 9.26 (s, 1H), 8.83-8.81 (m, 1H), 8.41-8.37 (m, 1H), 7.53-7.48 (m, 1H), 6.17-6.14 (m, 1H), 4.94-4.92 (m, 1H), 4.08-4.05 (m, 2H), 2.45-2.38 (m, 1H), 2.32-2.25 (m, 1H), 2.06-1.97 (m, 2H), 1.84-1.16 (m, other aliphatic ring protons), 1.03 (s, 6H), 0.96 (s, 6H), 0.92 (s, 3H), 0.90 (s, 3H), 0.85 (d, 3H, J = 6.6 Hz), 0.75 (d, 3H, J = 6.9 Hz). |
| C17 | 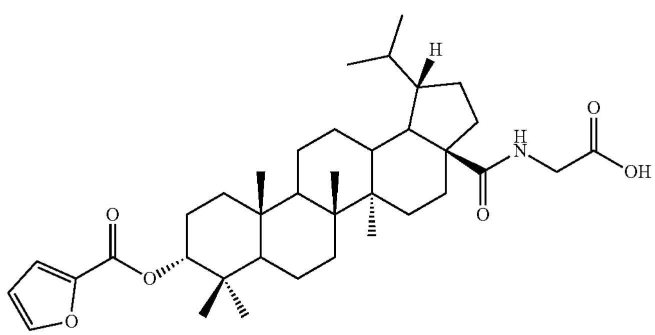 | ¹H NMR (300 MHz, CDCl₃) δ 7.59 (s, 1H), 7.13 (d, 1H, J = 3.3 Hz), 6.52-6.50 (m, 1H), 6.14 (t, 1H, J = 5.4 Hz), 4.85 (s, 1H), 4.07-4.05 (m, 2H), 2.44-2.36 (m, 1H), 2.32-2.24 (m, 1H), 2.06-1.15 (m, other aliphatic ring protons), 1.03 (s, 6H), 0.95 (s, 6H), 0.93 (s, 3H), 0.90-0.85 (m, 9H), 0.75 (d, 3H, J = 6.6 Hz). |
| C24 | 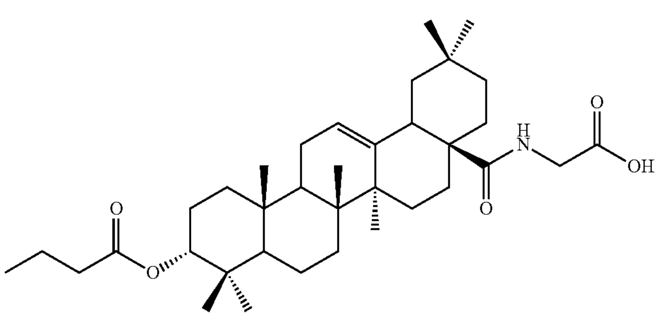 | ¹H NMR (300 MHz, CDCl₃) δ 6.69-6.66 (m, 1H), 5.48-5.46 (m, 1H), 4.65-4.63 (m, 1H), 4.09 (dd, J = 17.7, 5.4 Hz, 1H), 3.90 (dd, J = 17.7, 5.4 Hz, 1H), 2.60-2.56 (m, 1H), 2.31 (t, J = 7.5 Hz, 2H), 2.10-1.06 (m, other aliphatic ring protons), 0.99-0.85 (m, 18H), 0.74 (s, 3H). |

| Compound | Structure | NMR |
|---|---|---|
| C25 | 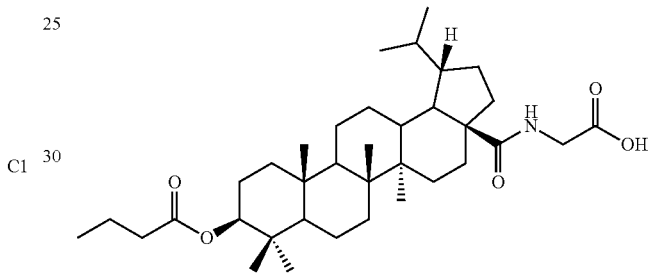 | $^1$H NMR (300 MHz, CDCl$_3$) δ 6.67-6.65 (m, 1H), 5.42-5.40 (m, 1H), 4.65 (s, 1H), 4.06 (dd, J = 17.7, 5.1 Hz, 1H), 3.90 (dd, J = 18.0, 4.2 Hz, 1H), 2.60-2.56 (m, 1H), 2.32 (t, J = 7.5 Hz, 2H), 2.05-1.06 (m, other aliphatic ring protons), 0.99-0.89 (m, 15H), 0.85 (s, 3H), 0.74 (s, 3H). |

EXAMPLE 2

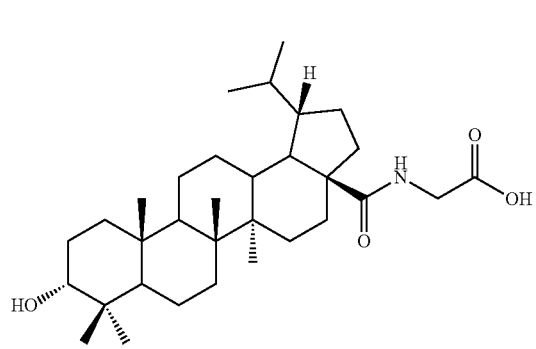

C1

Compound C4 (42 mg, 0.07 mmol) was dissolved in a mixed solvent of methanol and water (4:1) and sodium hydroxide (28 mg, 0.7 mmol) was added at 0° C. After 10 min, the mixture was warmed to room temperature and stirred for 12 hours. TLC showed that the reaction was complete. Methanol was removed by rotary evaporation and pH was adjusted to neutral with diluted hydrochloric acid. The mixture was diluted with ethyl acetate. Then the organic phase was washed separately with water and aqueous saturated sodium chloride solution, dried and concentrated over anhydrous sodium sulfate, and separated by column chromatography using an eluent system of dichloromethane/methanol (10:1) to obtain product C1 (21 mg, 0.04 mmol) in a molar yield of 57%. $^1$H NMR (300 MHz, CDCl$_3$) δ 6.13-6.10 (m, 1H), 4.04 (d, 2H, J=4.8 Hz), 3.40 (t, 1H, J=3.0 Hz), 2.43-1.12 (m, other aliphatic ring protons), 0.97 (s, 3H), 0.93 (s, 3H), 0.92 (s, 3H), 0.87-0.82 (m, 9H), 0.75 (d, 3H, J=6.9 Hz).

EXAMPLE 3

C12

(1) Compound S3 (148 mg, 0.27 mmol) and a catalytic amount of DMAP (3.7 mg, 0.03 mmol) were dissolved in dichloromethane (5 mL) and triethylamine (112 μL, 0.81 mmol) was added. Butyric anhydride (132 μL, 0.81 mmol) was added dropwise under an ice-water bath and the mixture was reacted at room temperature. After 12 hours, TLC showed that the reaction was complete. After the solvent was removed by concentration, the residue was diluted with ethyl acetate. The organic phase was washed separately with water and aqueous saturated sodium chloride solution, dried and concentrated over anhydrous sodium sulfate, and separated by column chromatography using an eluent system of petroleum ether/ethyl acetate (10:1) to obtain product S6 (142 mg, 0.23 mmol) in a molar yield of 85%. $^1$H NMR (300 MHz, CDCl$_3$) δ 7.37-7.30 (m, 5H), 5.15-5.05 (m, 2H), 4.50-4.45 (m, 1H), 2.34-2.14 (m, 4H), 1.86-1.09 (m, other aliphatic ring protons), 0.99-0.92 (m, 6H), 0.85-0.79 (m, 9H), 0.75-0.73 (m, 6H).

(2) The product S6 (142 mg, 0.23 mmol) was dissolved in methanol (15 mL) and a small amount of ethyl acetate. After the nitrogen was charged, 10% Pd/C was quickly added, then the nitrogen was charged and then hydrogen was charged. The mixture was stirred at room temperature for 1 hour and TLC detection showed that the reaction was complete. After the nitrogen was charged, Pd/C was filtered off, and the reaction solution was dried by rotary evaporation. The residue was separated by column chromatography using an eluent system of petroleum ether/ethyl acetate (8:1) to obtain compound S7 (101 mg, 0.19 mmol) as a white solid in a molar yield of 83%. $^1$H NMR (300 MHz, CDCl$_3$) δ 4.48 (t, 1H, J=7.5 Hz), 2.28 (t, 2H, J=7.5 Hz), 2.30-2.15 (m, 4H), 1.90-1.07 (m, other aliphatic ring protons), 0.94 (s, 3H), 0.91 (s, 3H), 0.90 (t, 3H, J=6.0 Hz), 0.85 (s, 3H), 0.83 (s, 3H), 0.82 (s, 3H), 0.75 (s, 3H), 0.73 (s, 3H).

(3) The product S7 (101 mg, 0.19 mmol) and a catalytic amount of DMF (2 μL, 0.02 mmol) were dissolved in 2 mL dried dichloromethane and oxalyl chloride (158 μL, 1.9 mmol) was added at 0° C. After 10 min, the mixture was warmed to room temperature and stirred for 3 hours. Dichloromethane was directly removed by rotary evaporation and the residue was dried with an oil pump and then used in next reaction. Tert-butyl glycinate hydrochloride (65 mg, 0.38 mmol) and a catalytic amount of DMAP (3.7 mg, 0.03 mmol) were dissolved in 1 mL dichloromethane. Triethylamine (130 μL, 0.95 mmol) was added dropwise at 0° C. and then 1 mL freshly prepared solution of acyl chloride in dichloromethane was added dropwise. After 10 min, the mixture was warmed to room temperature and stirred for 12 hours. TLC showed that the reaction was complete. After the solvent was removed by concentration, the residue was diluted with ethyl acetate. The organic phase was washed separately with water and aqueous saturated sodium chloride solution, dried and concentrated over anhydrous sodium sulfate, and separated by column chromatography using an eluent system of petroleum ether/ethyl acetate (8:1) to obtain product S8 (105 mg, 0.17 mmol) in a molar yield of 89%. $^1$H NMR (300 MHz, CDCl$_3$) δ 6.01 (t, 1H, J=5.1 Hz), 4.51-4.45 (m, 1H), 3.91-3.88 (m, 2H), 2.48-2.38 (m, 1H), 2.30-2.25 (m, 3H), 2.03-2.00 (m, 1H), 1.81-1.11 (m, other aliphatic ring protons), 1.47 (s, 9H), 0.97-0.91 (m, 9H), 0.86-0.83 (m, 12H), 0.74 (d, 3H, J=6.6 Hz).

(4) The product S8 (105 mg, 0.17 mmol) was dissolved in 5 mL dichloromethane and 0.2 mL TFA was added and stirred at room temperature for 1 hour. TLC showed that the reaction was complete. The solvent was directly removed by rotary evaporation and the residue was separated by column chromatography using an eluent system of dichloromethane/methanol (20:1) to obtain product C12 (82 mg, 0.14 mmol) in a molar yield of 82%. $^1$H NMR (300 MHz, CDCl$_3$) δ 6.15-6.11 (m, 1H), 4.51-4.45 (m, 1H), 4.05 (t, 1H, J=4.8 Hz), 2.38-2.25 (m, 4H), 2.02-1.12 (m, other aliphatic ring protons), 0.97-0.90 (m, 9H), 0.86-0.83 (m, 12H), 0.75 (d, 3H, J=6.6 Hz).

EXAMPLE 4 dried dichloromethane and oxalyl chloride (125 μL, 0.95 mmol) was added at 0° C. After 10 min, the mixture was warmed to room temperature and stirred for 3 hours. Dichloromethane was directly removed by rotary evaporation and the residue was dried with an oil pump and then used in next reaction. Tert-butyl glycinate hydrochloride (36 mg, 0.19 mmol) and a catalytic amount of DMAP (2.4 mg, 0.02 mmol) were dissolved in 1 mL dichloromethane and triethylamine (67 μL, 0.48 mmol) was added dropwise at 0° C. Then 1 mL freshly prepared solution of acyl chloride in dichloromethane was added dropwise. After 10 min, the mixture was warmed to room temperature and stirred for 12 hours. TLC showed that the reaction was complete. After the solvent was removed by concentration, the residue was diluted with ethyl acetate. The organic phase was washed separately with water and aqueous saturated sodium chloride solution, dried and concentrated over anhydrous sodium sulfate, and separated by column chromatography using an eluent system of petroleum ether/ethyl acetate (15:1) to obtain the product (47 mg, 0.072 mmol) in a molar yield of 76%. $^1$H NMR (300 MHz, CDCl$_3$) δ 6.18 (d, 1H, J=7.2 Hz), 4.62 (t, 1H, J=3.0 Hz), 4.48-4.38 (m, 1H), 2.44-2.27 (m, 4H), 2.01-1.03 (m, other aliphatic ring protons), 0.99-0.92 (m, 9H), 0.86-0.82 (m, 12H), 0.74 (d, 3H, J=6.6 Hz).

(2) The product obtained in the previous step (47 mg, 0.072 mmol) was dissolved in 2 mL dichloromethane and 0.2 mL TFA was added. The mixture was stirred at room temperature for 1 hour. TLC showed that the reaction was complete. The solvent was directly removed by rotary evaporation and the residue was separated by column chromatography using an eluent system of dichloromethane/methanol (20:1) to obtain product C18 (36 mg, 0.060 mmol) in a molar yield of 83%. $^1$H NMR (300 MHz, CDCl$_3$) δ 6.06 (d, 1H, J=6.6 Hz), 4.63 (s, 1H), 4.59-4.49 (m, 1H), 2.41-2.28 (m, 4H), 2.00-1.08 (m, other aliphatic ring protons), 1.00-0.93 (m, 9H), 0.88-0.83 (m, 12H), 0.75 (d, 3H, J=6.6 Hz).

Compound C19 was synthesized using D-alanine hydrochloride by using the same method as Example 4.

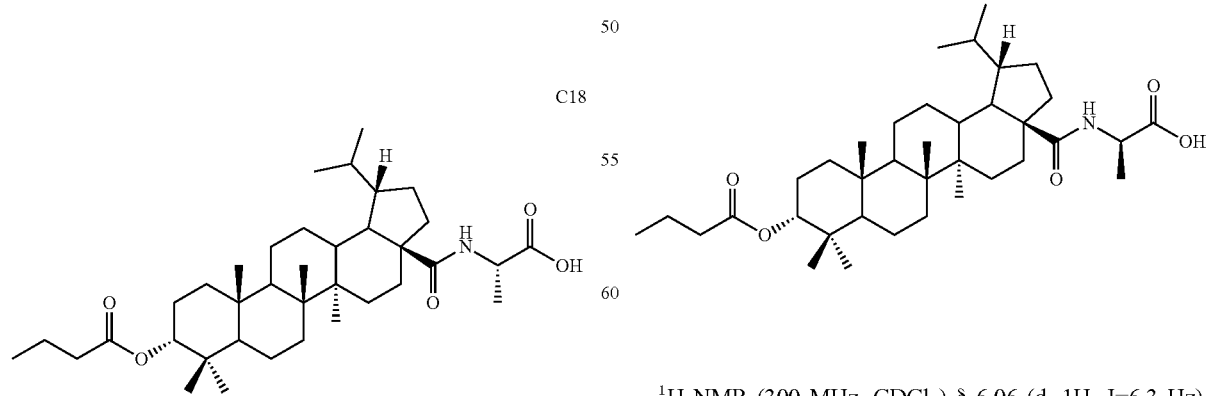

C18

(1) The product S10 (50 mg, 0.095 mmol) and a catalytic amount of DMF (1 μL, 0.01 mmol) were dissolved in 1 mL $^1$H NMR (300 MHz, CDCl$_3$) δ 6.06 (d, 1H, J=6.3 Hz), 4.63 (t, 1H, J=3.0 Hz), 4.55-4.46 (m, 1H), 2.43-2.24 (m, 4H), 2.03-1.05 (m, other aliphatic ring protons), 1.00-0.92 (m, 9H), 0.87-0.83 (m, 12H), 0.75 (d, 3H, J=6.6 Hz).

EXAMPLE 5

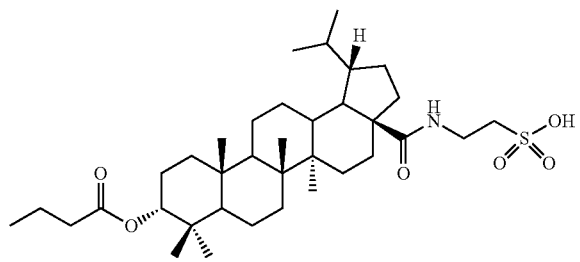

C20

Compound S10 (50 mg, 0.095 mmol) and a catalytic amount of DMF (1 μL, 0.01 mmol) were dissolved in 2 mL dried dichloromethane, and oxalyl chloride (80 μL, 0.95 mmol) was added at 0° C. After 10 min, the mixture was warmed to room temperature and stirred for 3 hours. Dichloromethane was directly removed by rotary evaporation and the residue was dried with an oil pump and then used in next reaction. The freshly prepared acyl chloride and triethylamine (263 μL, 1.9 mmol) were dissolved in dioxane (3 mL), then 1 mL aqueous solution of taurine (36 mg, 0.285 mmol) and triethylamine (263 μL, 1.9 mmol) was added dropwise at 0° C. After 10 min, the mixture was warmed to room temperature and stirred for 3 hours. TLC showed that the reaction was complete. The mixture was adjusted with diluted hydrochloric acid to acidic pH and diluted with ethyl acetate. The organic phase was washed separately with water and aqueous saturated sodium chloride solution, dried and concentrated over anhydrous sodium sulfate, and separated by column chromatography using an eluent system of dichloromethane/methanol (10:1) to obtain product C20 (16 mg, 0.025 mmol) in a molar yield of 27%. $^1$H NMR (300 MHz, CDCl$_3$) δ 7.09 (br s, 1H), 4.61 (s, 1H), 3.20-3.03 (m, 4H), 2.33-2.28 (m, 2H), 1.72-1.60 (m, 4H), 1.44-1.07 (m, other aliphatic ring protons), 0.99-0.89 (m, 9H), 0.87-0.81 (m, 12H), 0.73-0.72 (m, 3H).

EXAMPLE 6

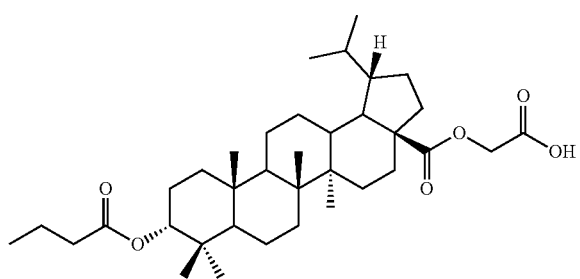

C21

(1) Compound S10 (100 mg, 0.189 mmol) was dissolved in ultra-dry DMF (3 mL), anhydrous potassium carbonate (65.3 mg, 0.473 mmol) was added, and benzyl bromoacetate (0.148 mL, 0.945 mmol) was slowly added dropwise with stirring. After addition, the mixture was stirred at room temperature for 3 hours. TLC monitoring showed that the reaction was complete. The mixture was diluted with 30 mL of deionized water and extracted with ethyl acetate (2×30 mL). The combined organic layers were washed separately with deionized water and saturated brine, dried and concentrated over sodium sulfate, and separated by column chromatography using an eluent system of petroleum ether/ethyl acetate (30:1) to obtain product S13 (124 mg, 0.183 mmol) in a molar yield of 97%. $^1$H NMR (300 MHz, CDCl$_3$) δ 7.38-7.34 (m, 5H), 5.24-5.13 (m, 2H), 4.63-4.62 (m, 3H), 2.32 (t, 2H, J=7.5 Hz), 2.28-2.20 (m, 2H), 1.96-1.77 (m, 3H), 1.71-1.64 (m, 2H), 1.61-1.04 (m, other aliphatic ring protons), 1.00-0.92 (m, 9H), 0.87-0.83 (m, 9H), 0.75 (d, 3H, J=6.9 Hz).

(2) The product S13 (124 mg, 0.183 mmol) was dissolved in methanol (15 mL) and a small amount of ethyl acetate. After the nitrogen was charged, 10% Pd/C was quickly added, then the nitrogen was charged and then hydrogen was charged. The mixture was stirred at room temperature. After 1 hour, TLC detection showed that the reaction was complete. After the nitrogen was charged, Pd/C was filtered off, and the reaction solution was dried by rotary evaporation and then separated by column chromatography using an eluent system of dichloromethane/methanol (20:1) to obtain compound C21 (80 mg, 0.137 mmol) as a white solid in a molar yield of 75%. $^1$H NMR (300 MHz, CDCl$_3$) δ 4.66-4.58 (m, 3H), 2.32 (t, 2H, J=7.5 Hz), 2.24-2.17 (m, 3H), 1.94-1.77 (m, 4H), 1.71-1.64 (m, 2H), 1.61-1.04 (m, other aliphatic ring protons), 1.00-0.92 (m, 9H), 0.87-0.82 (m, 9H), 0.75 (d, 3H, J=6.6 Hz).

EXAMPLE 7

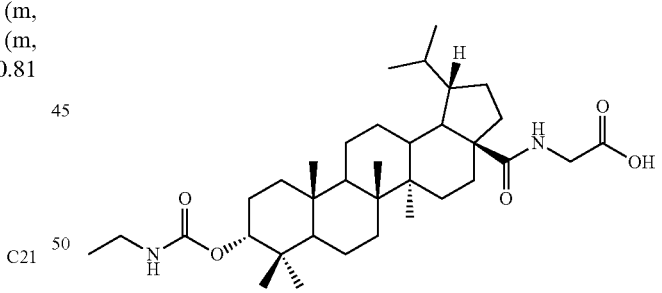

C22

(1) Compound SS (100 mg, 0.182 mmol), ethyl isocyanate (150 μL, 1.82 mmol), triethylamine (505 μL, 3.64 mmol) and DMAP (1.22 mg, 0.01 mmol) were dissolved in 3 mL of toluene. The tube was sealed and the mixture was reacted at 120° C. for two days. TLC monitoring showed that the reaction was complete. The mixture was diluted with 30 mL of deionized water and extracted with ethyl acetate (2×30 mL). The combined organic layers were washed separately with deionized water and saturated brine, dried and concentrated over sodium sulfate, and separated by column chromatography using an eluent system of petroleum ether/ethyl acetate (15:1) to obtain product S14 (85 mg, 0.137 mmol) in a molar yield of 75%. $^1$H NMR (300

MHz, CDCl$_3$) δ 7.37-7.26 (m, 5H), 5.15-5.06 (m, 2H), 4.64 (br s, 1H), 4.49 (s, 1H), 3.24-3.20 (m, 2H), 2.31-2.15 (m, 4H), 1.85-1.77 (m, 4H), 1.68-1.01 (m, other aliphatic ring protons), 0.96 (s, 3H), 0.86-0.82 (m, 12H), 0.75-0.73 (m, 6H).

(2) The product S14 (85 mg, 0.137 mmol) was dissolved in methanol (15 mL) and a small amount of ethyl acetate. After the nitrogen was charged, 10% Pd(OH)$_2$/C was quickly added, then the nitrogen was charged and then hydrogen was charged. The mixture was stirred at room temperature. After 1 hour, TLC detection showed that the reaction was complete. After the nitrogen was charged, Pd(OH)$_2$/C was filtered off. The reaction solution was dried by rotary evaporation and then separated by column chromatography using an eluent system of petroleum ether/ethyl acetate (8:1) to obtain compound S15 (61 mg, 0.115 mmol) as a white solid in a molar yield of 84%. $^1$H NMR (300 MHz, CDCl$_3$) δ 4.67 (br s, 1H), 4.50 (s, 1H), 3.27-3.17 (m, 2H), 2.29-2.16 (m, 4H), 1.91-1.78 (m, 4H), 1.68-1.06 (m, other aliphatic ring protons), 0.99 (s, 3H), 0.93 (s, 3H), 0.86-0.85 (m, 12H), 0.75 (d, 3H, J=6.9 Hz).

(3) The product S15 (61 mg, 0.115 mmol) and a catalytic amount of DMF (1 μL, 0.01 mmol) were dissolved in 2 mL dried dichloromethane and oxalyl chloride (96 μL, 1.15 mmol) was added at 0° C. After 10 min, the mixture was warmed to room temperature and stirred for 3 hours. Dichloromethane was directly removed by rotary evaporation and the residue was dried with an oil pump and then used in next reaction. Benzyl glycinate hydrochloride (47 mg, 0.23 mmol) and a catalytic amount of DMAP (2.4 mg, 0.02 mmol) were dissolved in 1 mL dichloromethane and triethylamine(80 μL, 0.58 mmol) was added dropwise at 0° C. Then 1 mL freshly prepared solution of acyl chloride in dichloromethane was added dropwise. After 10 min, the mixture was warmed to room temperature and stirred for 12 hours. TLC showed that the reaction was complete. After the solvent was removed by concentration, the residue was diluted with ethyl acetate. The organic phase was washed separately with water and aqueous saturated sodium chloride solution, dried and concentrated over anhydrous sodium sulfate, and separated by column chromatography using an eluent system of petroleum ether/ethyl acetate (8:1) to obtain product S16 (52 mg, 0.077 mmol) in a molar yield of 67%. $^1$H NMR (300 MHz, CDCl$_3$) δ 7.37-7.34 (m, 5H), 6.07 (t, 1H, J=5.4 Hz), 5.22-5.13 (m, 2H), 4.65 (br s, 1H), 4.49 (s, 1H), 4.08-3.97 (m, 2H), 3.26-3.17 (m, 2H), 2.46-2.23 (m, 3H), 2.03-1.04 (m, other aliphatic ring protons), 0.97 (s, 3H), 0.90 (s, 1H), 0.85-0.83 (m, 9H), 0.74 (d, 3H, J=6.9 Hz)

(4) The product S16 (52 mg, 0.077 mmol) was dissolved in methanol (10 mL) and a small amount of ethyl acetate. After the nitrogen was charged, 10% Pd/C was quickly added, then the nitrogen was charged and then hydrogen was charged. The mixture was stirred at room temperature. After 1 hour, TLC detection showed that the reaction was complete. After the nitrogen was charged, Pd/C was filtered off, and the reaction solution was dried by rotary evaporation and then separated by column chromatography using an eluent system of dichloromethane/methanol (20:1) to obtain compound C22 (38 mg, 0.065 mmol) in a molar yield of 84%. $^1$H NMR (300 MHz, CDCl$_3$) δ 6.17 (s, 1H), 4.66 (br s, 1H), 4.50 (s, 1H), 4.04-3.97 (m, 2H), 3.28-3.20 (m, 2H), 2.44-2.27 (m, 3H), 2.04-1.05 (m, other aliphatic ring protons), 0.98 (s, 3H), 0.92 (s, 3H), 0.86-0.84 (m, 9H), 0.74 (d, 3H, J=6.6 Hz)

EXAMPLE 8

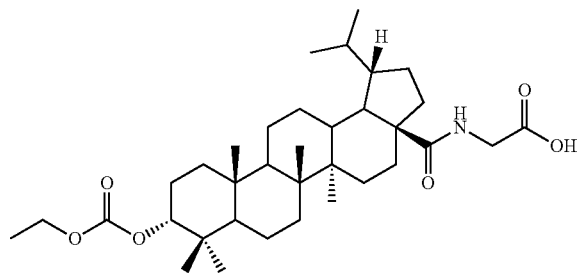

C23

(1) Compound S5 (130 mg, 0.237 mmol) was dissolved in 3 mL of pyridine, and ethyl chloroformate (113 μL, 1.19 mmol) was added at −20° C. After 10 minutes, the mixture was warmed to room temperature and stirred. After 2 hours, TLC detection showed that the reaction was complete. The mixture was diluted with 30 mL of deionized water and extracted with ethyl acetate (2×30 mL). The combined organic layers was washed separately with dilute hydrochloric acid, deionized water and saturated brine, dried over sodium sulfate, and separated by column chromatography using an eluent system of petroleum ether/ethyl acetate (10:1) to obtain product S17 (97 mg, 0.156 mmol) in a molar yield of 66%. $^1$H NMR (300 MHz, CDCl$_3$) δ 7.38-7.30 (m, 5H), 5.15-5.06 (m, 2H), 4.46 (t, 1H, J=2.7 Hz), 4.19 (q, 2H, J=7.2 Hz), 2.30-2.14 (m, 4H), 1.96-1.02 (m, other aliphatic ring protons), 0.95 (s, 3H), 0.90-0.83 (m, 15H), 0.75-0.73 (m, 6H).

(2) Compound S17 (97 mg, 0.156 mmol) was dissolved in methanol (20 mL) and a small amount of ethyl acetate. After the nitrogen was charged, 10% Pd(OH)$_2$/C was quickly added, then the nitrogen was charged and then hydrogen was charged. The mixture was stirred at room temperature. After 1 hour, TLC detection showed that the reaction was complete. After the nitrogen was charged, Pd(OH)$_2$/C was filtered off, and the reaction solution was dried by rotary evaporation and then separated by column chromatography using an eluent system of petroleum ether/ethyl acetate (8:1) to obtain compound S18 (48 mg, 0.091 mmol) as a white solid in a molar yield of 58%. $^1$H NMR (300 MHz, CDCl$_3$) δ 4.47 (t, 1H, J=2.7 Hz), 4.20 (q, 2H, J=7.2 Hz), 2.28-2.14 (m, 4H), 1.91-1.14 (m, other aliphatic ring protons), 0.98 (s, 3H), 0.93 (s, 3H), 0.90 (s, 3H), 0.88-0.84 (m, 9H), 0.75 (d, 3H, J=6.9 Hz).

(3)The product S18 (48 mg, 0.091 mmol) and a catalytic amount of DMF (1 μL, 0.01 mmol) were dissolved in 2 mL dried dichloromethane and oxalyl chloride (76 μL, 0.91 mmol) was added at 0° C. After 10 min, the mixture was warmed to room temperature and stirred for 3 hours. Dichloromethane was directly removed by rotary evaporation and the residue was dried with an oil pump and then used in next reaction. Benzyl glycinate hydrochloride (37 mg, 0.18 mmol) and a catalytic amount of DMAP (2.4 mg, 0.02 mmol) were dissolved in 1 mL dichloromethane and triethylamine (64 μL, 0.46 mmol) was added dropwise at 0° C. Then 1 mL freshly prepared solution of acyl chloride in dichloromethane was added dropwise. After 10 min, the mixture was warmed to room temperature and stirred for 12 hours. TLC showed that the reaction was complete. After the solvent was removed by concentration, the residue was diluted with ethyl acetate. The organic phase was washed separately with water and aqueous saturated sodium chloride solution, dried and concentrated over anhydrous sodium sulfate, and separated by column chromatography using an eluent system of petroleum ether/ethyl acetate (8:1) to obtain product S19 (49 mg, 0.072 mmol) in a molar yield of 79%. $^1$H NMR (300 MHz, CDCl$_3$) δ 7.37-7.35 (m, 5H), 6.04 (t, 1H, J=5.4 Hz), 5.22-5.14 (m, 2H), 4.47 (t, 1H, J=2.7 Hz), 4.19 (q, 2H, J=7.2 Hz), 4.05 (d, 2H, J=5.4 Hz), 2.46-2.37 (m, 1H), 2.31-2.23 (m, 1H), 2.02-1.10 (m, other aliphatic ring protons), 0.97 (s, 3H), 0.90-0.83 (m, 15H), 0.74 (d, 3H, J=6.9 Hz).

(4) The product S19 (49 mg, 0.072 mmol) was dissolved in methanol (10 mL) and a small amount of ethyl acetate. After the nitrogen was charged, 10% Pd/C was quickly added, then the nitrogen was charged and then hydrogen was charged. The mixture was stirred at room temperature. After 1 hour, TLC detection showed that the reaction was complete. After the nitrogen was charged, Pd/C was filtered off, and the reaction solution was dried by rotary evaporation and then separated by column chromatography using an eluent system of dichloromethane/methanol (20:1) to obtain compound C23 (35 mg, 0.060 mmol) in a molar yield of 83%. $^1$H NMR (300 MHz, CDCl$_3$) δ 6.15 (t, 1H, J=5.4 Hz), 4.46 (t, 1H, J=2.7 Hz), 4.19 (q, 2H, J=7.2 Hz), 4.05-4.03 (m, 2H), 2.42-2.32 (m, 1H), 2.29-2.21 (m, 1H), 2.02-1.12 (m, other aliphatic ring protons), 0.97 (s, 3H), 0.91-0.84 (m, 12H), 0.74 (d, 3H, J=6.9 Hz).

EXAMPLE 9 FXR ANTAGONIST TEST

1. Experiment Purpose

The antagonistic activity of the compound against FXR was detected by the reporter gene experiment.

2. Experiment Principle

FXR is a nuclear receptor activated by bile acids and has regulatory effects on glucose metabolism and lipid metabolism in the body. After FXR is activated, it can initiate the expression of a series of genes and respond to external stimuli. The Luciferase reporter gene system is a reporting system for detecting firefly luciferase activity. Luciferase can catalyze the oxidation of Luciferin, a fluorescent substrate, and cause emition of biological fluorescence at the same time. The amount of luciferase expression can be determined by detecting the fluorescence intensity. In this experiment, the test compound may target FXR, and GW4064 is a known FXR agonist, which initiates the expression of a series of genes after binding to the FXR ligand-binding domain. Therefore, the reporter gene experiment was used. Two plasmids, LBD (hFXR)-pbind and PGL4.31-Luc were co-transfected into HEK293 cells to express the FXR ligand-binding domain in the cells. Two test compounds were separately added and a blank control group was set, and then an agonist was added. If the compound has affinity for FXR, it will compete with the agonist for binding to the FXR ligand-binding domain and affect the expression of luciferase in pGL4.31-Luc. The Envision2101 multi-well microplate reader was used to detect the chemiluminescence count value, and the effect of the test compound on FXR activity was judged based on the fluorescence intensity.

3. Experiment Sample

Before the test, the compound was dissolved in DMSO to prepare a mother liquor, and the culture solution was used to dilute it to the required concentration.

4. Experiment Method

2 μg of the chimeric plasmid LBD(hFXR)-pbind and 2 μg of Luciferase reporter plasmid were co-transfected into $2 \times 10^6$ HEK293 cells and inoculated in white opaque 96-well plates. After 24 h, the culture medium was discarded, and the test compound (diluted with serum-free culture medium, containing 1% DMSO) was added and incubated for 1 h. Then FXR agonist GW4064 (300 nM) was added to stimulate for 6 h, and finally luciferase substrate was added and shaken to lyse. Luminescence was measured on the Envision 2104 microplate reader.

5. Experiment Results: (Six Compounds Such as C1 Were Used as Examples, But Not Limited to These Compounds)

TABLE 1

Test results of antagonistic activities of compounds against FXR

| Compound No. | FXR(IC$_{50}$/μM) |
|---|---|
| C1 | 13.95 |
| C2 | 6.31 |
| C3 | 3.89 |
| C4 | 2.05 |
| C12 | 8.27 |
| C16 | 5.67 |

Note:
IC$_{50}$ is the evaluation of antagonistic activities of samples against FXR, half (50%) effective concentration.

6. Results and Discussion

These compounds can compete with FXR agonist GW4064 in HEK293 cells expressing the FXR ligand-binding domain, and antagonize the activation of FXR by GW4064. Their activity is dose-dependent, and IC$_{50}$ values are shown in Table 1. The results indicate that these compounds are antagonists of the FXR receptor.

EXAMPLE 10 TGR5 AGITATION TEST EXAMPLE

1. Experiment Purpose

HEK293 cells transiently transfected with TGR5 were stimulated with compounds, and then homogeneous time-resolved fluorescence (HTRF) was used to detect whether these compounds could agitate TGR5.

2. Experiment Principle

TGR5 is a bile acid membrane receptor and a member of the GPCR family. It regulates the metabolism of bile acids, lipids, and sugars. TGR5 is coupled to the Gs protein, and after activation, it further activates adenylate cyclase to produce a second messenger cAMP. HTRF is a method for detecting the content of cAMP and combines two techniques of fluorescence resonance energy transfer (FRET) and time-resolved fluorescence (TRF). The emission spectrum of Eu-containing cave compound as a fluorescent donor has a certain overlap with fluorescence acceptor excitation spectrum. FRET induces the acceptor to generate fluorescence, and Eu has a long fluorescence lifetime. TRF can distinguish the fluorescent signal by the acceptor from the fluorescent background. The fluorescent donor is bound to a cAMP-specific antibody, and cAMP is simultaneously labeled with a fluorescent acceptor. The donor and acceptor approach to each other through the antigen-antibody specific recognition reaction to generate FRET, and the cAMP produced by the cell competes with the labeled cAMP for antibody binding sites, resulting in the decrease of fluorescence intensity. In this experiment, TGR5 agonist INT777 is used as a positive control to investigate the effect of compounds on TGR5.

3. Experiment Sample

Before the test, the compound was dissolved in DMSO to prepare a mother liquor, and the culture solution was used to dilute it to the required concentration.

4. Experiment Method 4.1. The test compound was prepared with 1× PBS into a solution having 2 times of the final concentration. The final concentration was 100 μM, 10 μM, 1 μM, 100 nM, 10 nM, 1 nM, 0.1 nM, DMSO (each well contains 1% DMSO).
4.2 Cell processing
4.2.1. Cells were digested with trypsin and resuspended in serum-free culture.
4.2.2. The cell density was determined. At the same time, IBMX (final concentration of 500 mM) was added into the serum-free culture medium, and the number of cells was 2000/5 μl/well.
4.2.3. 5 μl of the test compound and 5 μl of the cell suspension containing IBMX were added and mixed. A 384-well plate was sealed with a foil paper. The mixtures were protected from light and reacted at room temperature for less than 30 minutes.
4.3. Preparation of detection substrate
4.3.1 1 μl cAMP-d2 was diluted to 20 μl by using cAMP&cGMP conjugates & lysis buffer. 4.3.2 1 μl anti-cAMP-Cryptate was diluted to 20 μl by using cAMP&cGMP conjugates&lysis buffer.
4.3.3 After 30 minutes, 5 μl (1.3.1) and 5 μl (1.3.2) were added and a 384-well plate was sealed with a foil paper. The mixtures were protected from light and reacted at room temperature.
4.4. After 60 minutes, the values were detected by Envision 2101 microplate reader (PerkinElmer).

5. Experiment Results (Six compounds such as C1 were used as examples, but not limited to these compounds)

TABLE 2

Test results of TGR5 agonistic activity of compounds

| Compound No. | FXR (IC$_{50}$/μM) |
|---|---|
| INT777 | 50.46 |
| C1 | NR |
| C2 | NR |

TABLE 2-continued

Test results of TGR5 agonistic activity of compounds

| Compound No. | FXR (IC$_{50}$/μM) |
|---|---|
| C3 | NR |
| C4 | NR |
| C12 | NR |
| C16 | NR |

Note:
IC$_{50}$ is the evaluation of antagonistic activities of samples against FXR, half (50%) effective concentration.
NR indicates no activity at a concentration of 100 μM.

6. Results and Discussion

These compounds are unable to increase intracellular cAMP accumulation in HEK293 cells expressing TGR5. Table 2 shows that the compounds have selective antagonistic effects on FXR.

EXAMPLE 11 CCK-8 TEST EXAMPLE

1. Experiment Purpose

The cytotoxicity of the compounds was evaluated by using CCK-8 experiment.

2. Experiment Principle

CCK-8 is an indicator of redox reaction. In the presence of the electron carrier 1-Methoxy PMS, dehydrogenase in living cells is used to catalyze the tetrazolium salt WST-8 to form formazan dye. The production amount of formazan dye has a linear relationship with the number of living cells. The light absorption value measured at 450 nm using a microplate reader can indirectly reflect the number of living cells. Therefore, this method is used for the activity detection of some bioactive factors, large-scale anti-tumor drug screening, cell proliferation test, cytotoxicity test, and drug sensitivity test. This experiment is used to evaluate the cytotoxicity of the compounds.

3. Experiment Sample

Before the test, the compound was dissolved in DMSO to prepare a mother liquor, and the culture solution was used to dilute it to the required concentration.

4. Experiment Method

2 μg of the chimeric plasmid LBD(hFXR)-pbind and 2 μg of Luciferase reporter plasmid were co-transfected into 2×10$^6$ HEK293 cells and inoculated in transparent 96-well plates. After 24 h, the culture medium was discarded and the test compound (diluted in serum-free culture medium, containing 1% DMSO) was added and incubated for 1 h, then FXR agonist GW4064 (300 nM) was added to agitate for 4 h. 10 μl detection reagent for CCK-8 was added to each well. After 2 hours, absorbance values at 450 nm and 650 nm (as reference wavelength) were detected with Flextation instrument.

5. Experiment Results: (Six Compounds Such as C1 Were Used as Examples, But Not Limited to These Compounds)

TABLE 3

Test results of compound CCK-8

| Compound No. | CCK-8 Assay (30 μM) | CCK-8 Assay (100 μM) |
|---|---|---|
| C1 | no | no |
| C2 | no | no |
| C3 | no | no |
| C4 | no | no |
| C12 | no | no |
| C16 | no | no |

6. Results and Discussion

The experiment results in table 3 show that these compounds have no obvious toxicity on HEK293 cells at 30 μM and 100 μM concentrations.

All documents mentioned in the present invention are incorporated by reference in this application, as each document is individually incorporated by reference. In addition, it should be understood that after reading the above-mentioned teaching content of the present invention, those skilled in the art can make various changes or modifications to the present invention, and these equivalent forms also fall within the scope defined by the appended claims of the present application.

The invention claimed is:

1. A compound or pharmaceutically acceptable salt thereof, wherein the compound is:

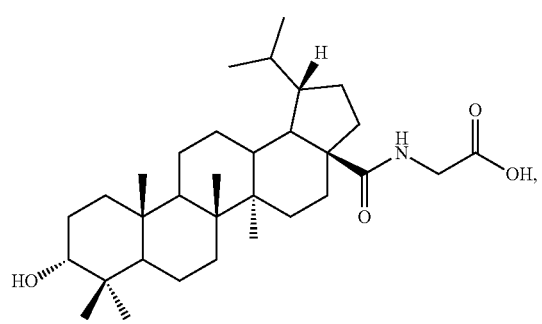

C1

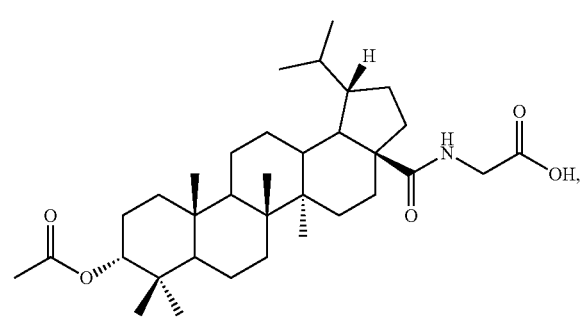

C2

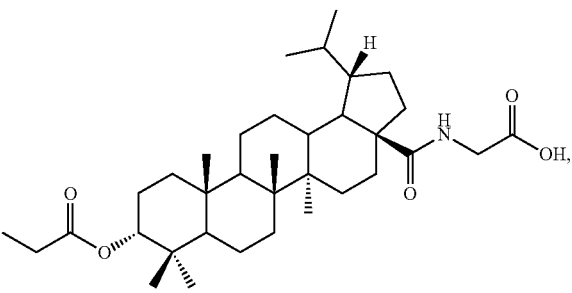

C3

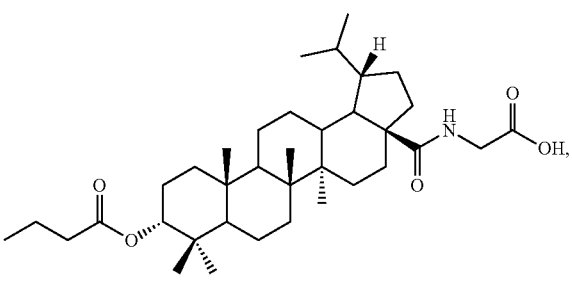

C4

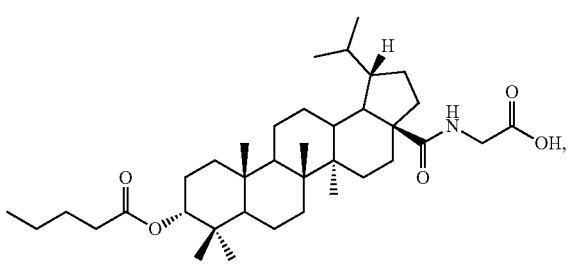

C5

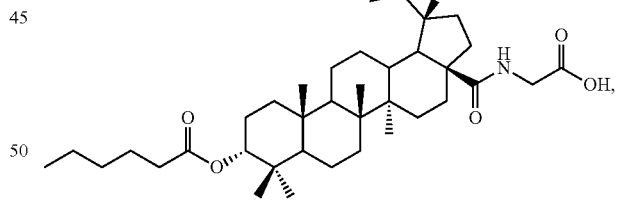

C6

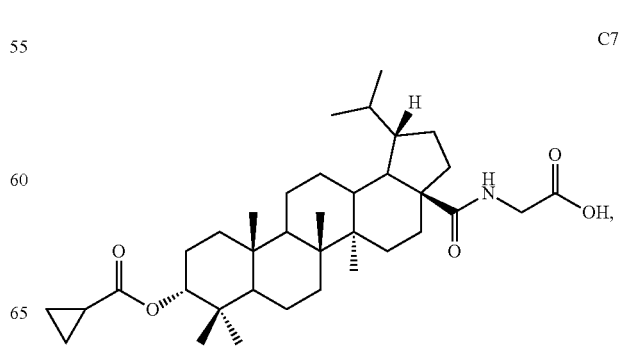

C7

-continued
C8
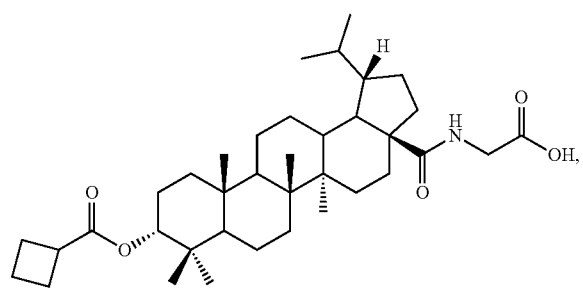
C9
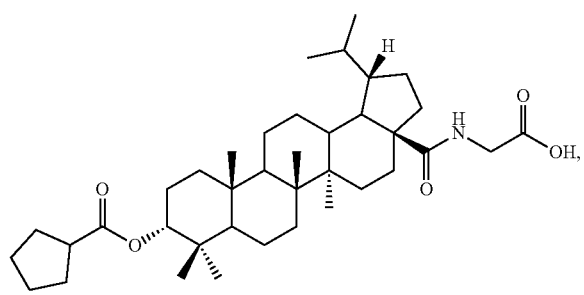
C10
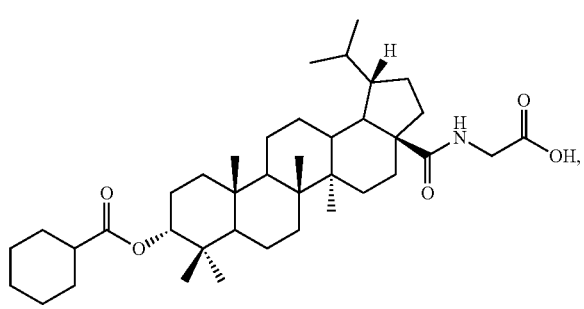
C11
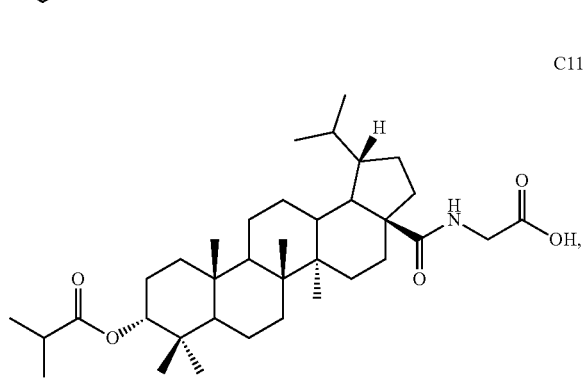
C12
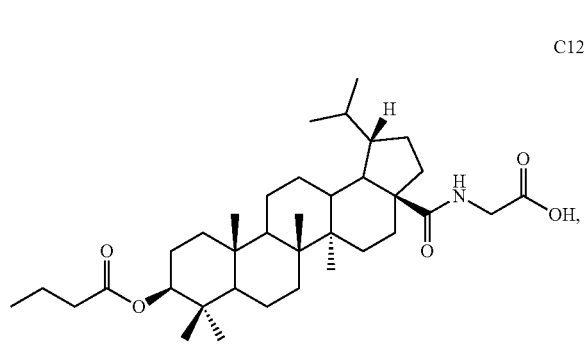
-continued
C13
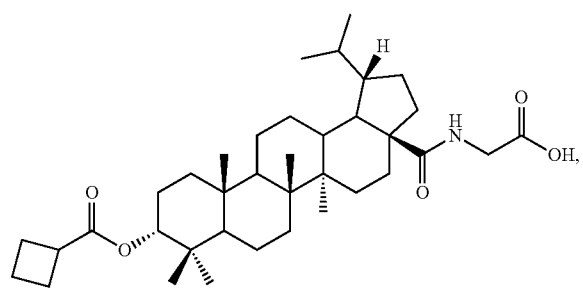
C14
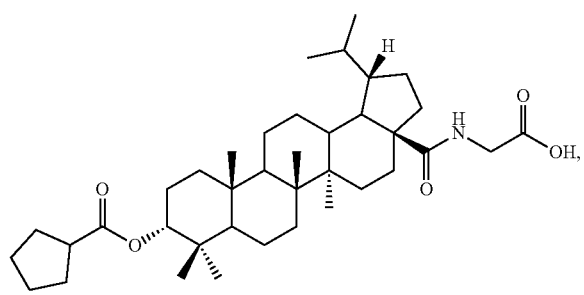
C15
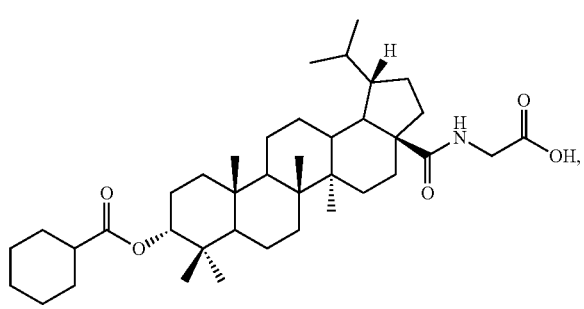
C16
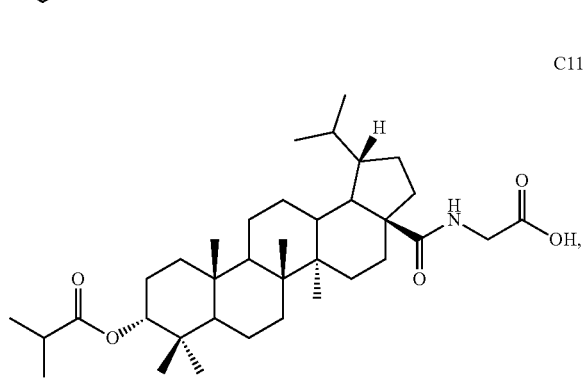
C17
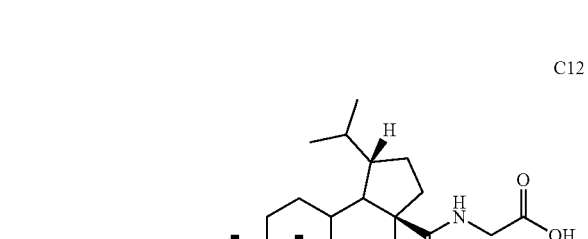

C18
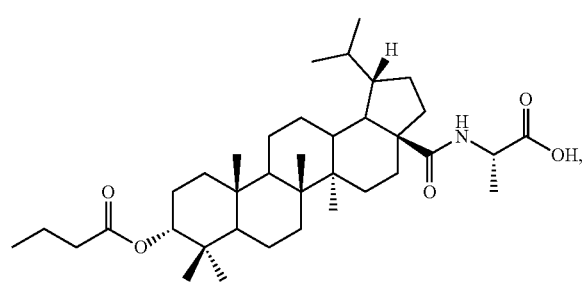

C19
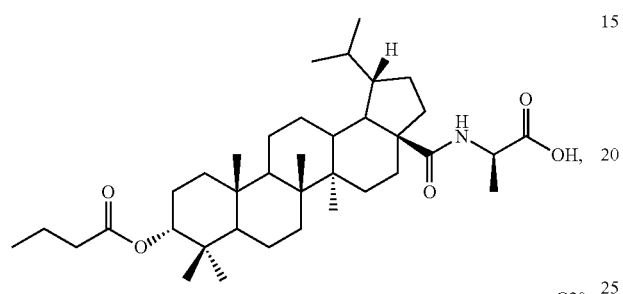

C20
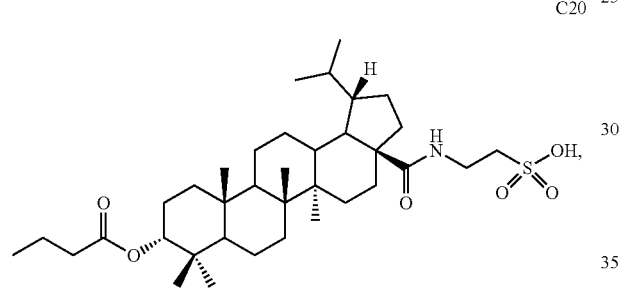

C21
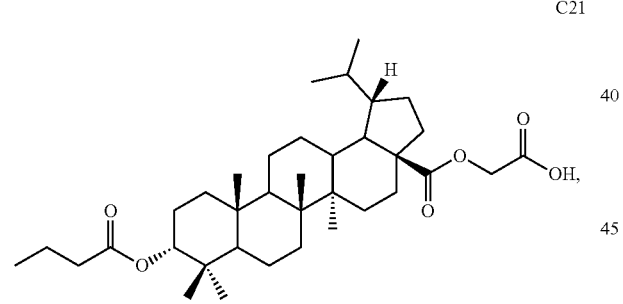

C22
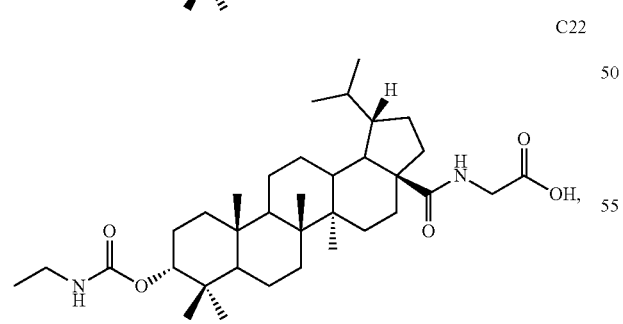

C23
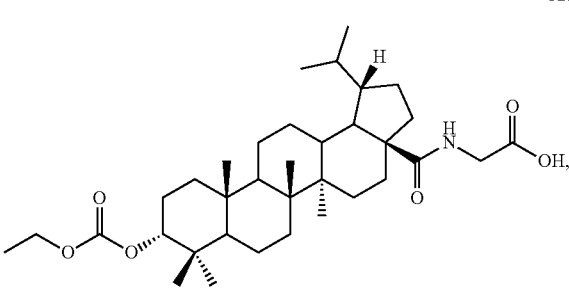

C24
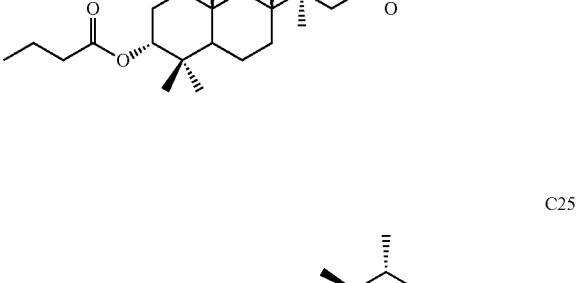

or

C25
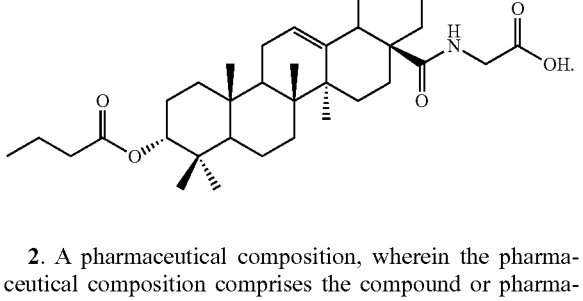

2. A pharmaceutical composition, wherein the pharmaceutical composition comprises the compound or pharmaceutically acceptable salt thereof of claim 1; and a pharmaceutically acceptable carrier.

3. A method for antagonizing a farnesoid X receptor (FXR) comprising administering the compound or the pharmaceutically acceptable salt thereof according to claim 1 to a subject in need thereof.

4. A method for treating a metabolic disease comprising administering the compound or the pharmaceutically acceptable salt thereof according to claim 1 to a subject in need thereof.

* * * * *